(12) United States Patent
Bannae et al.

(10) Patent No.: US 11,085,981 B2
(45) Date of Patent: Aug. 10, 2021

(54) MAGNETIC RESONANCE IMAGING APPARATUS FOR GENERATING T1 MAP HAVING HIGHLY ACCURATE T1 VALUES

(71) Applicant: Canon Medical Systems Corporation, Otawara (JP)

(72) Inventors: Shuhei Bannae, Utsunomiya (JP); Shigeharu Ohyu, Yaita (JP)

(73) Assignee: Canon Medical Systems Corporation, Otawara (JP)

( * ) Notice: Subject to any disclaimer, the term of this patent is extended or adjusted under 35 U.S.C. 154(b) by 162 days.

(21) Appl. No.: 16/419,155

(22) Filed: May 22, 2019

(65) Prior Publication Data

US 2019/0369188 A1 Dec. 5, 2019

(30) Foreign Application Priority Data

Jun. 4, 2018 (JP) .............................. JP2018-106849
May 13, 2019 (JP) .............................. JP2019-090734

(51) Int. Cl.
*G01R 33/50* (2006.01)
*A61B 5/055* (2006.01)
*G01R 33/54* (2006.01)
*G01R 33/56* (2006.01)

(52) U.S. Cl.
CPC .............. *G01R 33/50* (2013.01); *A61B 5/055* (2013.01); *G01R 33/543* (2013.01); *G01R 33/5602* (2013.01)

(58) Field of Classification Search
CPC ...... A61B 5/055; A61B 5/7285; G01R 33/50; G01R 33/543; G01R 33/5602; G01R 33/546; G01R 33/5673
See application file for complete search history.

(56) References Cited

U.S. PATENT DOCUMENTS

| 9,129,424 B2 | 9/2015 | Xue et al. |
| 9,285,446 B2 | 3/2016 | Piechnik et al. |
| 2006/0161060 A1* | 7/2006 | Pai ....................... G01R 33/563 600/431 |

(Continued)

OTHER PUBLICATIONS

Messroghli, D. et al. "Modified Look-Locker Inversion Recovery (MOLLI) for High-Resolution $T_1$ Mapping of the Heart", Magnetic Resonance in Medicine vol. 52., 2004, pp. 141-146.

(Continued)

*Primary Examiner* — Jay Patidar
(74) *Attorney, Agent, or Firm* — Oblon, McClelland, Maier & Neustadt, L.L.P.

(57) ABSTRACT

According to one embodiment, an MRI apparatus includes sequence control circuitry and processing circuitry. The sequence control circuitry executes a pulse sequence for collecting MR signals in collection timings along a relaxation curve of longitudinal magnetization in synchronization with heartbeats or blood beats. The processing circuitry generate a T1 map representing a distribution of T1 values by using the collected MR signals. The pulse sequence is set so as not to collect any MR signal in at least one heartbeat or blood beat among heartbeats or blood beats included between first and second inversion pulses, and so as to collect an MR signal in a heartbeat or blood beat subsequent to the at least one heartbeat or blood beat in which no MR signal is collected.

20 Claims, 15 Drawing Sheets

(56) References Cited

U.S. PATENT DOCUMENTS

2014/0350385 A1  11/2014  Banerjee et al.
2018/0217217 A1* 8/2018  Weingartner ........ A61B 5/0044

OTHER PUBLICATIONS

Kellman, P., et al., "T1-mapping in the heart: accuracy and precision", Journal of Cardiovascular Magnetic Resonance, vol. 16. No. 2, 2014, pp. 1-20.

* cited by examiner

| Range of heart rate | Collection heart rate | Number of inversion times | TI (ms) (Take image in described order) | Collection pattern |
|---|---|---|---|---|
| Wide range (50~100 bpm) | One heartbeat collection | 5 | TI=70-102-150-218-319 | */**/-*/-*/** |
| | | 4 | TI=60-97-157-253 | */-**-*// ← MI2 |
| | | 3 | TI=60-126-265 | */-/*-*/** |
| | | 2 | TI=61-320 | */-/*/-*** |
| Low heart rate (50~75 bpm) | One heartbeat collection | 5 | TI=60-100-167-277-460 | */-*/*/*/-/ |
| | | 4 | TI=60-116-225-434 | */-*/*/--/* |
| | | 3 | TI=482-170-60 | */-*/*-*-/-*/* ← MI1 |
| | | 2 | TI=60-491 | */-*/-* |
| Mediate heart rate (60~85 bpm) | One heartbeat collection | 5 | TI=61-95-148-231-359 | */-**-*/*//*/* |
| | | 4 | TI=61-111-201-363 | */-***-*///* |
| | | 3 | TI=60-157-408 | */***-*// |
| | | 2 | TI=420-60 | */-/**-*/*** |
| High heart rate (75~100 bpm) | One heartbeat collection | 5 | TI=61-91-138-209-315 | */-*-*/*//**/*/* |
| | | 4 | TI=151-190-240-304 | */-/*-*-*/-/-/** |
| | | 3 | TI=143-211-313 | */-/*/*-*/**-* |
| | | 2 | TI=60-239 | */-/*/-* |
| High heart rate (75~90 bpm) | Two heartbeat collection | 5 | TI=75-125-208-346-575 | */*/*/*/*/* |
| | | 4 | TI=66-137-284-589 | */**/-*/*/* |
| | | 3 | TI=619-210-71 | */-***/*/* |
| | | 2 | TI=611-67 | *-// |

FIG. 4

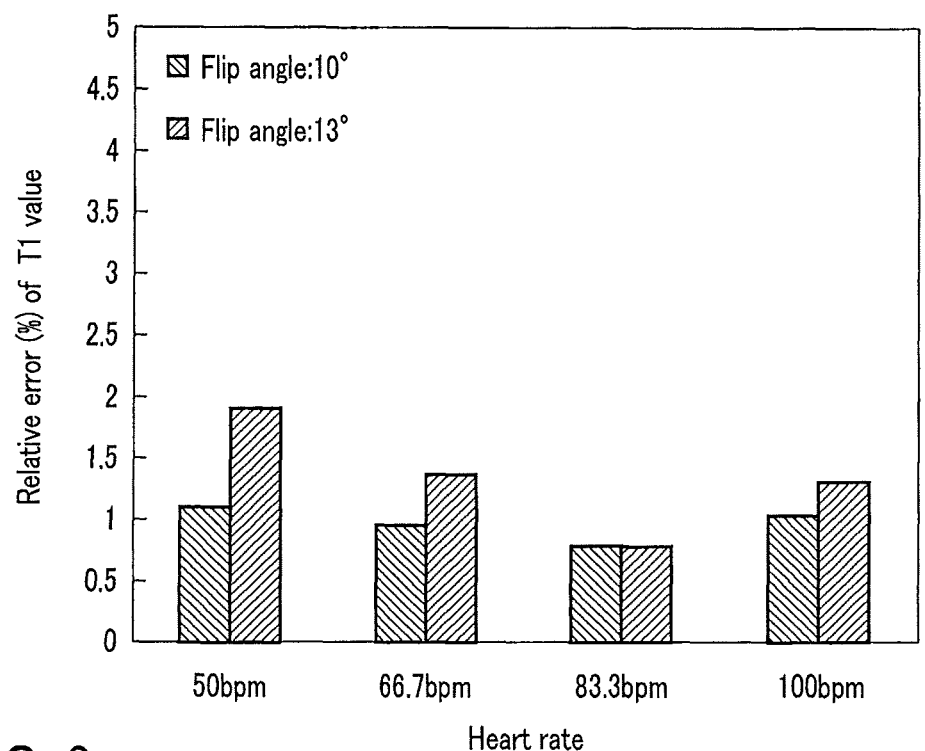
F I G. 6
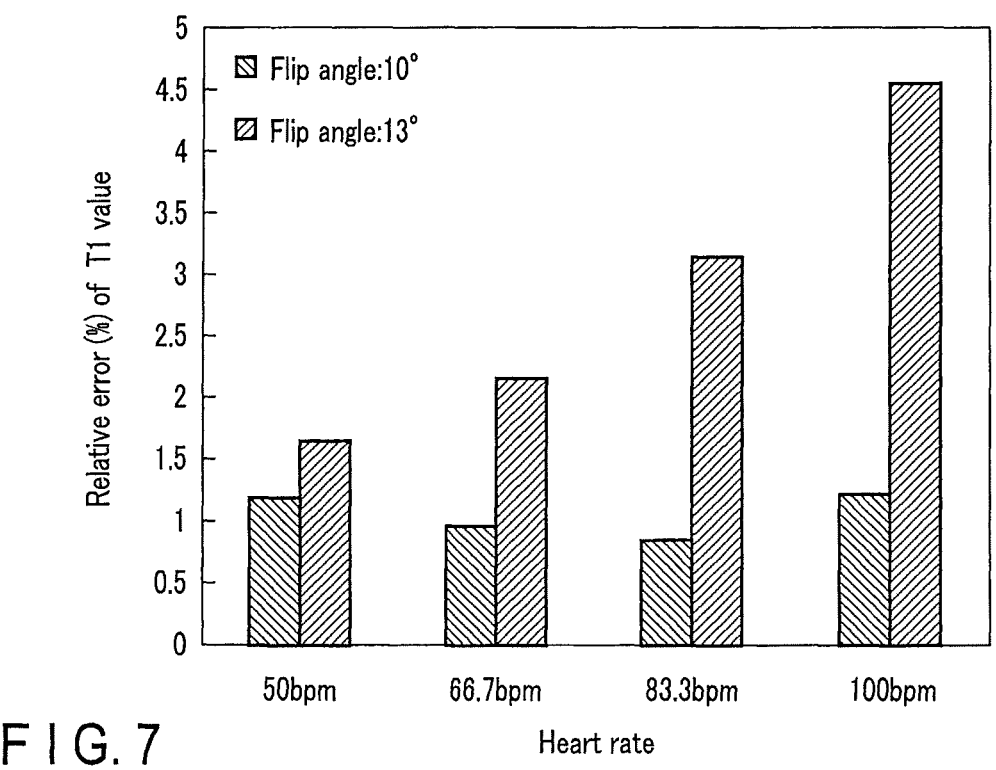
F I G. 7

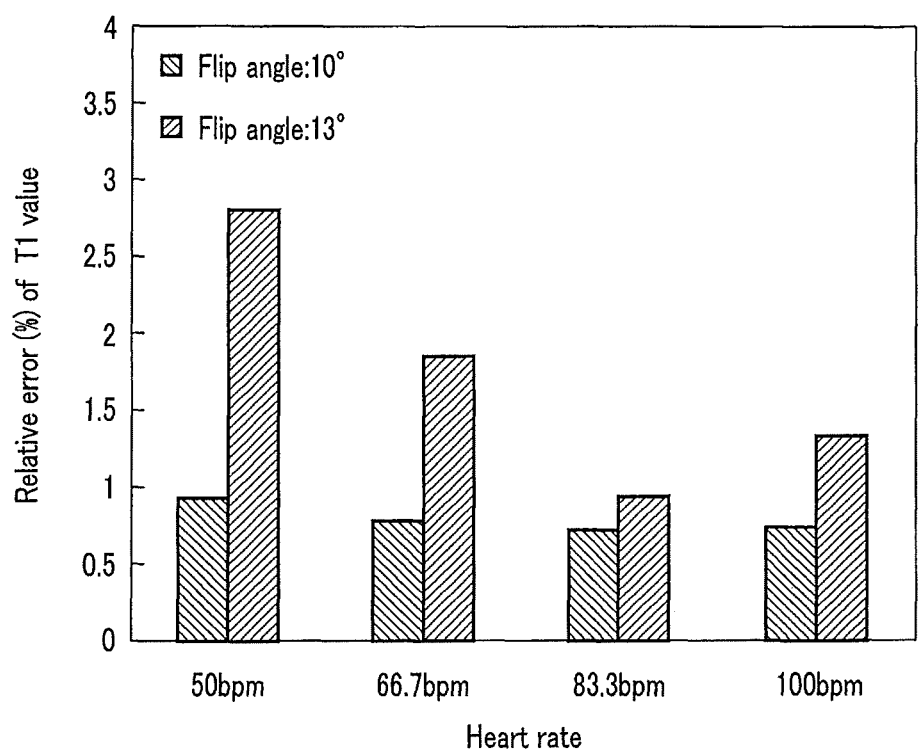
F I G. 8

MAGNETIC RESONANCE IMAGING APPARATUS FOR GENERATING T1 MAP HAVING HIGHLY ACCURATE T1 VALUES

CROSS-REFERENCE TO RELATED APPLICATIONS

This application is based upon and claims the benefit of priority from the prior Japanese Patent Applications No. 2018-106849, filed Jun. 4, 2018, and No. 2019-090734, filed May 13, 2019, the entire contents of all of which are incorporated herein by reference.

FIELD

Embodiments described herein relate generally to a magnetic resonance imaging apparatus.

BACKGROUND

Magnetic resonance imaging is an imaging method of magnetically exciting atomic nucleus spins of a subject, which is laid in a still magnetic field, using an RF signal of a Larmor frequency and reconstructing an image from an MR signal generated along with the excitation. In the field of magnetic resonance imaging, there exists a technique called "T1 mapping" that enables quantitatively imaging a longitudinal relaxation time (T1 value) of a tissue. In an Inversion Recovery method, which is one of imaging methods concerning T1 mapping, a pulse called an inversion recovery pulse which inverts longitudinal magnetization, is used. In the inversion recovery method, a plurality of pieces of data that differ in period of time (hereinafter, referred to as "TI" (inversion time)) from an inversion pulse to a data collection are obtained by repeating application of the inversion pulse and the data collection. A magnetic resonance imaging apparatus calculates a T1 value on a pixel to pixel basis by using the plurality of pieces of data and each inversion time of the plurality of pieces of data and obtains a T1 map.

As a typical technique for applying T1 mapping to a heart, there is a MOLLI (Modified Look-Locker Inversion Recovery) method. In the MOLLI method, after an inversion pulse is applied to a subject, imaging is performed over a plurality of heartbeats in the timing that the cardiac phase becomes identical, and data different in inversion time is collected. In the MOLLI method, the application of an inversion pulse is performed plural times, and a recovery time of longitudinal magnetization is provided after the collection of data such that the longitudinal magnetization is sufficiently recovered before the application of each of inversion pulses.

In the MOLLI method, the inversion time corresponding to each image depends on the number of heartbeats at the time of imaging. For this reason, there may be a case where data cannot be collected in a desired inversion time, and a distribution of data relative to the inversion time is biased. The inversion time, which depends on the number of heartbeats at the time of imaging, causes a degradation in the measurement accuracy of T1 values. When data is to be collected in a desired inversion time, the number of times an inversion pulse is applied may sometimes increase. In such a case, there is a problem that a period over which a breath is held (or a "breath-hold") is prolonged due to an extension of the imaging time, resulting in a burden on the subject.

FIG. 10 is a view illustrating a relaxation curve (ReL) of longitudinal magnetization in the MOLLI method, along with an electrocardiographic waveform. The relaxation curve ReL illustrated in FIG. 10 shows temporal changes in a relative value to a signal value (hereinafter, referred to as "relative signal value") obtained by a data collection according to the MOLLI method. As illustrated in FIG. 10, in the MOLLI method, since imaging is performed plural times after application of each inversion pulse, the longitudinal magnetization is attenuated under the influence of an RF pulse during the collection of data. The influence of attenuation of the longitudinal magnetization during a data collection is indicated, for example, by $\delta_{ro}$ shown in FIG. 10. Therefore, there is a problem that data (a signal value) in the next data collection represents a signal value lower than that shown in the original T1 relaxation curve, resulting in a degradation in the measurement accuracy of T1 values.

In addition, in the MOLLI method, there may be a case where a signal value does not increase in the ascending order of TI due to the influence of an RF pulse at the time of data collection and an insufficient recovery time of longitudinal magnetization. That is, as illustrated in FIG. 10, a relative signal value MS1 obtained by the data collection in an inversion time TI1 after a first inversion pulse may be sometimes greater than a relative signal value MS2 obtained by the data collection in an inversion time TI2 after a second inversion pulse. In FIG. 10, a difference between the relative signal value MS1 and the relative signal value MS2 is represented by $\delta_{rs}$. FIG. 11 is a view illustrating an example in which relative signal values of data collected by the MOLLI method are plotted against the TI (inversion times). As illustrated in FIG. 11, there may be a case where the relative signal value MS2 becomes smaller than the relative signal value MS1 by only the difference $\delta_{rs}$, but the relative signal values may not be increased monotonously in accordance with the inversion times. Therefore, there is a problem that the relative signal value does not increase in the ascending order of the inversion times, causing a failure of an inversion of the polarity of a signal value in the calculation process of a T1 value, which leads to a degradation of the calculation accuracy of the T1 value.

BRIEF DESCRIPTION OF THE DRAWING

FIG. 4 is a view illustrating an example of a plurality of T1 sequences respectively corresponding to a plurality of collection patterns in the embodiment.

FIG. 6 is a view illustrating an example of relative errors of T1 values when a T1 sequence MI2 using a flip angle of 10° or 13° is executed for different heart rates.

FIG. 7 is a view illustrating, as a comparative example, an example of relative errors of T1 values when a pulse sequence having the same inversion time as the inversion time in the T1 sequence MI2 in the embodiment, flip angle of 10° or 13°, and a collection pattern of "*/-**//**/*" is executed relative to different heart rates.

FIG. 8 is a view illustrating, as a comparative example, an example of relative errors of T1 values when a pulse sequence having the same inversion time as the inversion time in the T1 sequence MI2 in the embodiment, a flip angle of 10° or 13°, and a collection pattern of "*/***-*///*" is executed relative to different heart rates.

DETAILED DESCRIPTION

According to one embodiment, a magnetic resonance imaging apparatus includes sequence control circuitry and processing circuitry.

The sequence control circuitry executes a pulse sequence for collecting magnetic resonance signals in a plurality of collecting timings along a relaxation curve of longitudinal magnetization in synchronization of heartbeats or blood beats.

The processing circuitry generates a T1 map representing a distribution of T1 values by using the magnetic resonance signals collected in the plurality of collection timings.

The pulse sequence is set so as not to collect any magnetic resonance signal in at least one heartbeat or at least one blood beat among a plurality of heartbeats or a plurality of blood beats included between a first inversion pulse which inverts a polarity of the longitudinal magnetization and a second inversion pulse which is applied after applying the first inversion pulse, and so as to collect a magnetic resonance signal in a heartbeat or a blood beat subsequent to the at least one heartbeat or the at least one blood beat in which no magnetic resonance signal is collected.

An object is to generate a T1 map having highly accurate T1 values.

Hereinafter, embodiments of a magnetic resonance imaging apparatus (hereinafter, referred to as MRI apparatus) will be described with reference to drawings. In the following description, structural elements having substantially the same functions and configurations are provided with the same reference signs, and overlapping descriptions will be provided when necessary.

Embodiment

Figure 1:
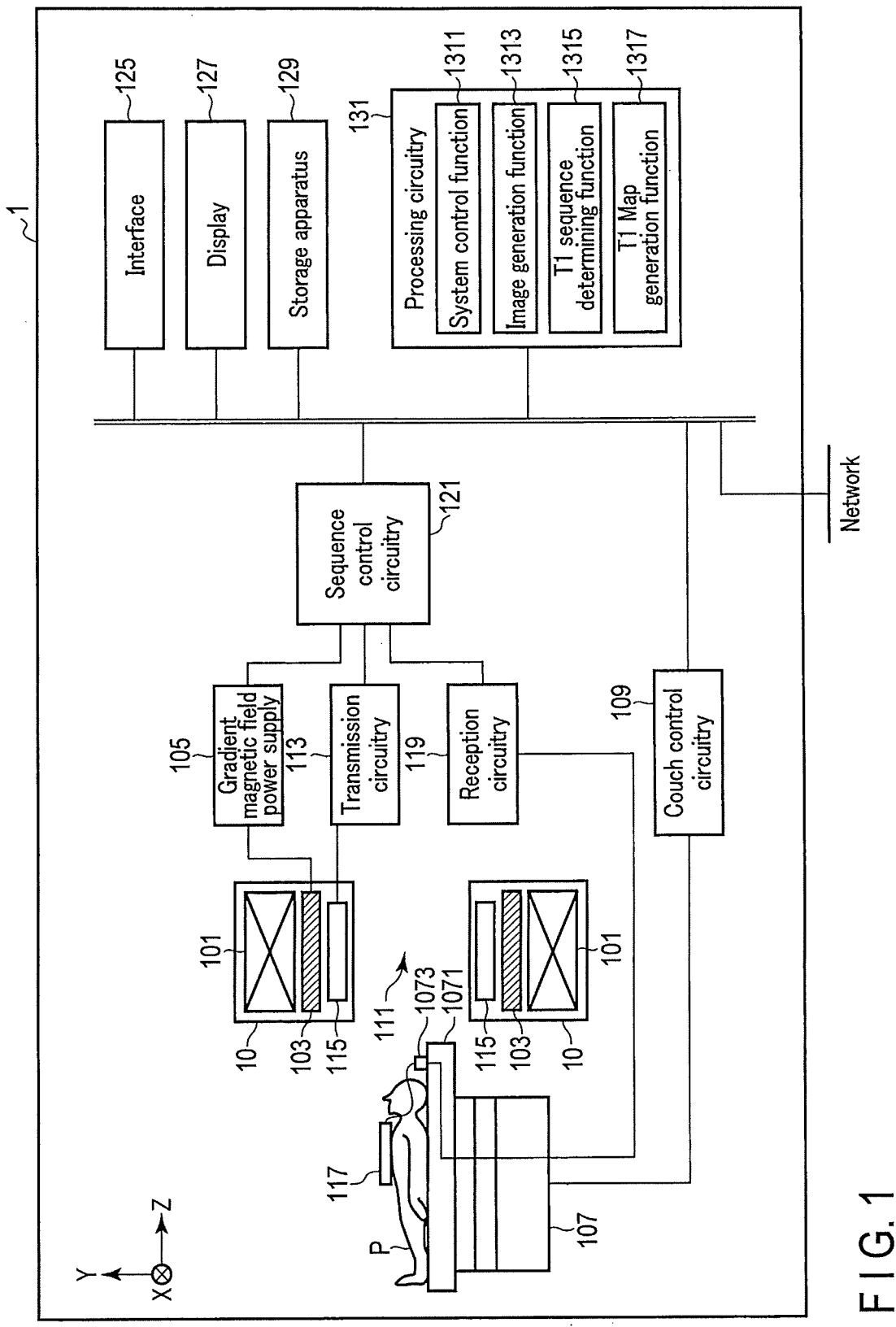
FIG. 1 is a block view illustrating the entire configuration of a magnetic resonance imaging apparatus according to an embodiment.

FIG. 1 is a block view illustrating the entire configuration of an MRI apparatus 1 according to the embodiment. The MRI apparatus 1 includes a static field magnet 101, a gradient magnetic field coil 103, a gradient magnetic field power supply 105, a couch 107, couch control circuitry 109, transmission circuitry (transmission unit) 113, a transmit coil 115, a receive coil 117, reception circuitry (reception unit) 119, sequence control circuitry (sequence control unit) 121, an interface (accepting unit) 125, a display (display unit) 127, a storage apparatus (storage unit) 129, and processing circuitry (processing unit) 131. A pintle mount 10 in the MRI apparatus 1 includes the static field magnet 101, the gradient magnetic field coil 103, and the transmit coil 115. The pintle mount 10 may include a hollow cylinder-shaped shim coil between the static field magnet 101 and the gradient magnetic field coil 103.

The static field magnet 101 is a magnet formed, for example, in a hollow cylindrical shape. The static field magnet 101 generates a uniform static field in a bore 111 corresponding to a space into which a subject P is inserted. As the static field magnet 101, for example, a superconducting magnet, or the like is used.

The gradient magnetic field coil 103 is a coil formed, for example, in a hollow cylindrical shape. The gradient magnetic field coil 103 is disposed in the inside of the static field magnet 101. The gradient magnetic field coil 103 is formed by combining three coils corresponding to X-, Y- and Z-axes which are orthogonal to each other. The Z-axis direction is identical to the direction of the static magnetic field. In addition, the Y-axis direction is a vertical direction. The X-axis direction is a direction perpendicular to the Z-axis and Y-axis. The gradient magnetic field coil 103 generates a gradient magnetic field to be superposed on the static magnetic field. Specifically, the three coils in the gradient magnetic field coil 103 individually receive supply of currents from the gradient magnetic field power supply 105 and generate a gradient field with a field intensity varying along each of the X-, Y- and Z-axes.

The gradient fields of the X-, Y- and Z-axes, which are generated by the gradient magnetic field coil 103, form, for example, a frequency encode gradient magnetic field (also referred to as "readout gradient magnetic field"), a phase encode gradient field, and a slice selection gradient field. The frequency encode gradient magnetic field is utilized in order to vary the frequency of a magnetic resonance (hereinafter, referred to as "MR (Magnetic Resonance)") signal in accordance with a spatial position. The phase encode gradient field is utilized in order to vary the phase of the MR signal in accordance with a spatial position. The slice selection gradient field is utilized in order to determine an imaging cross section. In addition, the gradient fields of the X-, Y- and Z-axes generated by the gradient magnetic field coil 103 are used as re-convergence pulses in which the direction of the gradient magnetic field is inverted twice in order to make, for example, phases of spins on the X-Y plane re-converge.

The gradient magnetic field power supply 105 is a power supply device which supplies current to the gradient magnetic field coil 103 under the control of the sequence control circuitry 121.

The couch 107 is an apparatus which includes a couch top 1071 on which the subject P is placed. Under the control of the couch control circuitry 109, the couch 107 inserts the couch top 1071 on which the subject P is placed into the bore 111. The couch 107 is disposed in an inspection room such that the longitudinal direction of the couch 107 is parallel to the center axis of the static field magnet 101.

The couch top 1071 includes a plurality of coil ports to which the receive coil 117 can be connected. The subject P is placed on the couch top 1071. A connector provided at one end of a cable in the receive coil 117 is connected to one coil port 1073 of the plurality of coil ports. The location where the coil ports are arranged is not limited to the couch top 1071, and the coil ports may be provided in the couch 107, the pintle mount 10, or the like. A signal line from the coil port 1073 is connected to the reception circuitry 119. If the receive coil 117 has a transmission function with a high-frequency magnetic field, the signal line (not shown in FIG. 1) from the coil port 1073 is also connected to the transmission circuitry 113 in addition to the reception circuitry 119.

The couch control circuitry 109 is circuitry which controls the couch 107. The couch control circuitry 109 drives the couch 107 by means of instructions of the operator via the interface 125 to thereby move the couch top 1071 in the longitudinal direction, in the up-and-down direction, and in some situations, in the lateral direction.

The transmission circuitry 113 supplies high-frequency pulses modulated using a Larmor frequency to the transmit coil 115 by the control of the sequence control circuitry 121.

The transmit coil 115 is an RF coil disposed within the gradient magnetic field coil 103. The transmit coil 115 generates an RF (Radio Frequency) pulse corresponding to a high-frequency magnetic field in accordance with an output from the transmission circuitry 113. The transmit coil 115 is, for example, a coil for whole body (hereinafter, referred to as "WB (whole body) coil"). The WB coil may be used as a transmit/receive coil. Also, the transmit coil 115 may be a WB coil formed from one coil.

The receive coil 117 is an RF coil disposed within the gradient magnetic field coil 103. The receive coil 117 receives an MR signal radiated from the subject P by a high-frequency magnetic field and outputs the received MR signal to the reception circuitry 119. The receive coil 117 is, for example, a coil array including one or more, typically, a plurality of coil elements. It should be noted that FIG. 1 illustrates the transmit coil 115 and the receive coil 117 as separate RF coils; however, the transmit coil 115 and the receive coil 117 may be executed as an integrated transmit/receive coil. The transmit/receive coil corresponds to an imaging site of the subject P, for example, a local transmit/receive RF coil like a head coil.

The reception circuitry 119 generates a digital MR signal (hereinafter, referred to as "MR data"), based on the MR signal output from the receive coil 117 under the control of the sequence control circuitry 121. Specifically, the reception circuit 119 performs various kinds of signal processing for the MR signals output from the receive coil 117, and thereafter executes an analogue/digital (A/D (Analog to Digital)) conversion for data that has been subjected to the various kinds of signal processing. The reception circuitry 119 samples the A/D-converted data (sampling). With this configuration, the reception circuitry 119 creates MR data. The reception circuitry 119 outputs the created MR data to the sequence control circuitry 121.

The sequence control circuitry 121 controls the gradient magnetic field power supply 105, the transmission circuitry 113, and the reception circuitry 119 in accordance with an imaging protocol output from the processing circuitry 131, and takes images of the subject P. The imaging protocol includes various kinds of pulse sequences according to inspections. In the imaging protocol, the intensity of current supplied from the gradient magnetic field power supply 105 to the gradient magnetic field coil 103, the timing in which the current is supplied from the gradient magnetic field power supply 105 to the gradient magnetic field coil 103, the intensity or the time width of a high-frequency pulse supplied from the transmission circuitry 113 to the transmit coil 115, the timing in which the high-frequency pulse is supplied from the transmission circuitry 113 to the transmit coil 115, and the timing in which an MR signal is received by the receive coil 117 are set.

The interface 125 includes circuitry which accepts various kinds of instructions or entries of information from an operator. The interface 125 includes circuitry relating to, for example, a pointing device, such as a mouse, or an input device, such as a keyboard. It should be noted that the circuitry included in the interface 125 is not limited to circuitry relating to physical operational components, such as a mouse and a keyboard. For example, the interface 125 may include processing circuitry of such an electric signal that receives an electric signal corresponding to an input operation from an external input device which is provided separately from the MRI apparatus 1 and outputs the received electric signal to various kinds of circuitry. Bio-signal measuring devices (not shown) typified by an electrocardiograph, a sphygmograph, a phonocardiograph, a pulse counter, and a respiration sensor, external storage devices (not shown), and a network may be connected to the interface 125. For example, the interface 125 outputs, to the processing circuitry 131, an R wave of an electrocardiographic waveform transmitted from an ECG electrode attached to the subject P.

The display 127 is a display device, for example, a CRT display, a liquid crystal display, an organic EL display, an LED display, a plasma display, or other discretional display or monitor known in this technical field.

The display 127 displays, under the control of a system control function 1311 in the processing circuitry 131, various MR images generated by an image generation function 1313, a T1 sequence selected by a T1 sequence determining function 1315 (to be described later), a T1 map generated by a T1 map generation function 1317, and various kinds of information relating to imaging and image processing. The T1 map is an image in which a value (T1 value) of a relaxation time is provided on a pixel to pixel basis.

The T1 sequence is a pulse sequence to collect MR data in a plurality of timings along a relaxation curve of the longitudinal magnetization in synchronization with heartbeats or blood beats and is composed of a value of inversion time (TI) from an inversion pulse to a data collection, and a collection pattern. The T1 sequence is a pulse sequence which is executed for, for example, an organ showing a periodic movement, such as a heart, as an imaging target, to collect MR signals relating to generation of a T1 map. The collection pattern corresponds to a collection rule schematically showing imaging which is executed on a heartbeat or a blood beat before the initial inversion pulse of a plurality of inversion pulses which invert the polarity of the longitudinal magnetization in a T1 sequence (hereinafter, referred to as "pre-inversion imaging"); a heartbeat or a blood beat in which no MR data is collected in at least one heartbeat or at least one blood beat among a plurality of heartbeats or a plurality of blood beats after the initial inversion pulse (hereinafter, referred to as "non-read-out period"); and a plurality of inversion pulses which are executed without waiting for recovery of relaxation of the longitudinal magnetization (hereinafter, referred to as "unrelaxed IR pulses").

The storage apparatus 129 stores MR data supplied to a k-space via the image generation function 1313, image data generated by the image generation function 1313, a T1 map generated by the T1 map generation function 1317, and the like. In addition, the storage apparatus 129 stores a plurality of collection patterns according to a relation (hereinafter, referred to as "pulse relation") among heartbeats or blood beats, collection timings of MR signals, and an inversion pulse. The storage apparatus 129 stores imaging conditions, etc. including a plurality of imaging parameters that define an imaging protocol. The pulse relation corresponds to at least one imaging parameter in a T1 sequence. The storage apparatus 129 stores programs corresponding to various functions executed by the processing circuitry 131.

The storage apparatus 129 is, for example, a semiconductor memory device, such as RAM (Random Access Memory) and a flash memory; a hard disk drive; a solid state drive, or an optical disc. In addition, the storage apparatus 129 may be a drive which reads/writes various information from/to a portable storage medium.

The processing circuitry 131 includes, as hardware resources, a processor (not shown) and memories, such as a ROM (Read-Only Memory) and a RAM, to control the MRI apparatus 1. The processing circuitry 131 includes the system control function 1311, the image generation function 1313, the T1 sequence determining function 1315, and the T1 map generation function 1317. Various functions performed by the system control function 1311, image generation function 1313, T1 sequence determining function 1315, and T1 map generation function 1317 are stored in the storage apparatus 129 in the form of programs executable by a computer. The processing circuitry 131 is a processor that realizes a function corresponding to each program by reading out a program corresponding to each of these various functions from the storage apparatus 129 and executing the program. In other words, the processing circuitry 131 in a state of reading out various programs has a plurality of functions illustrated in the processing circuitry 131 in FIG. 1.

In FIG. 1, the embodiment is described in which these various functions are realized by single processing circuitry 131; however, a plurality of independent processors may be combined to structure processing circuitry 131 in such a manner that each of the processors realizes a function by executing a program. In other words, the processing circuitry 131 may be a case where the above described respective functions are configured as programs, and one processing circuitry executes each program, or may be a case where a specific function is mounted on dedicated independent program-executing circuitry.

The term "processor" used in the above description means, for example, a CPU (Central Processing Unit), a GPU (Graphics Processing Unit), or circuitry such as an ASIC (Application Specific Integrated Circuit), a programmable logic device (e.g. SPLD (Simple Programmable Logic Device), CLPD (Complex Programmable Logic Device), FPGA (Field Programmable Gate Array)), or the like.

The processor realizes various functions by reading out and executing the programs stored in the storage apparatus 129. In the meantime, instead of storing the programs in the storage apparatus 129, such a configuration may be adopted that the programs are directly incorporated in the circuitry in the processor. In this case, the processor realizes the functions by reading out and executing the programs incorporated in the circuitry in the processor. It should be noted that the couch control circuitry 109, the transmission circuitry 113, the reception circuitry 119, and the sequence control circuitry are similarly composed of electronic circuitry such as the above described processor. In the meantime, the system control function 1311, image generation function 1313, T1 sequence determining function 1315, and T1 map generation function 1317 included in the processing circuitry 131 are examples of a system controlling unit, an image generating unit, a T1 sequence determining unit, and a T1 map generating unit, respectively.

The processing circuitry 131 controls various types of circuitry in the MRI apparatus 1 by the system control function 1311. Specifically, the processing circuitry 131 reads out a system control program stored in the storage apparatus 129, develops the read-out control program on the memory, and controls each circuitry of the MRI apparatus 1 in accordance with the developed control program. For example, the processing circuitry 131 reads out an imaging protocol from the storage apparatus 129 by the system control function 1311, based on the image conditions entered by an operator via the interface 125. The processing circuitry 131 may be configured to generate an imaging protocol based on the imaging conditions. The processing circuitry 131 transmits the imaging protocol to the sequence control circuitry 121 and controls various kinds of imaging for a subject P.

The processing circuitry 131 fills MR data in a k-space by the image generation function 1313. The processing circuit 131 generates an MR image by performing the Fourier transform on the MR data filled in the k-space. The image generation function 1313, T1 sequence determining function 1315, and T1 map generation function 1317 will be described later.

Figure 2:
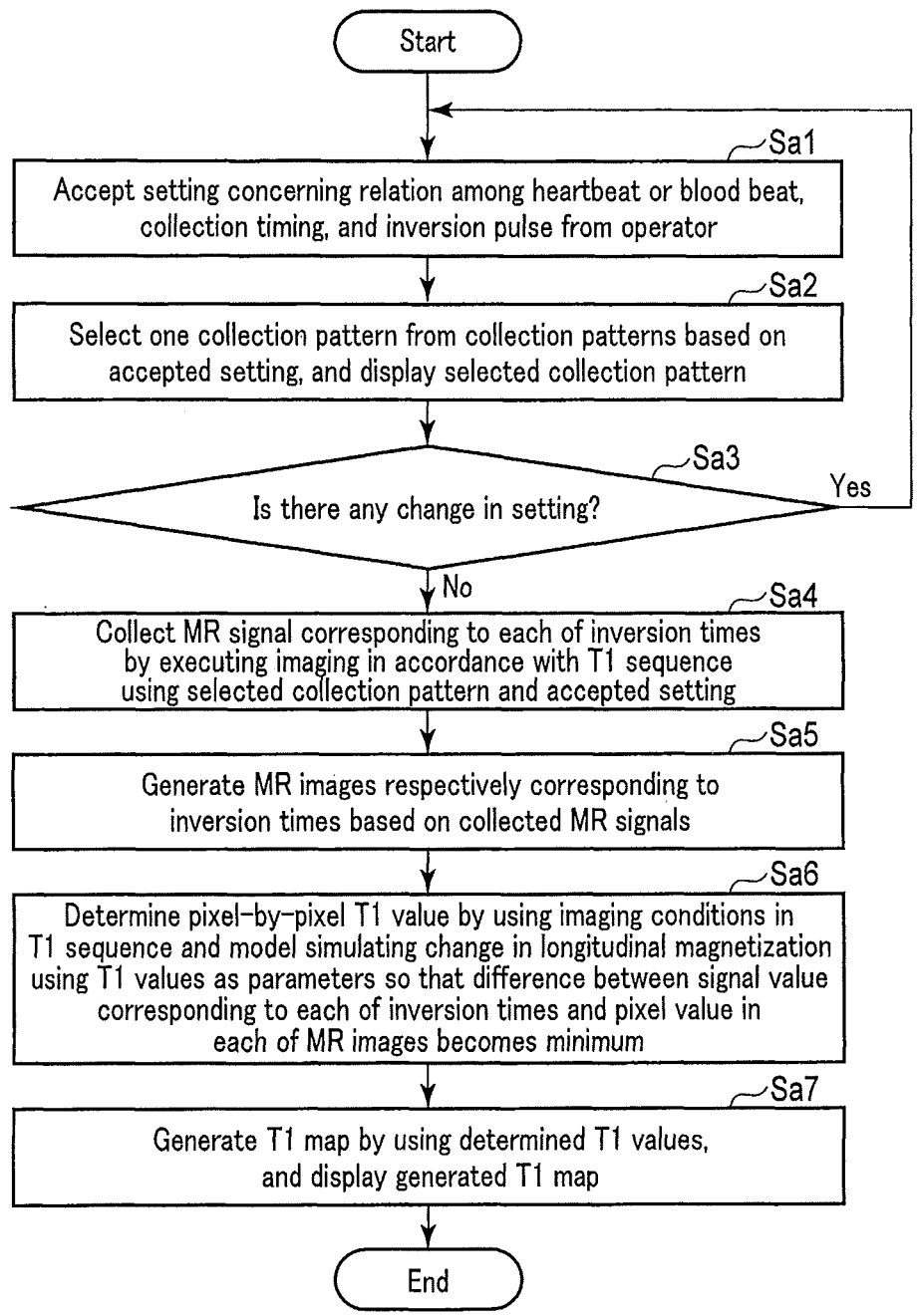
FIG. 2 is a flow chart illustrating an example of a procedure of T1 map generation processing in the embodiment.

The above descriptions are schematic descriptions of the entire configuration of the MRI apparatus 1 in the embodiment. Hereinafter, the processing including imaging relating to the generation of a T1 map according to the present embodiment (hereinafter, referred to as "T1 map generation processing) will be explained. Prior to the execution of the T1 map generation processing, the interface 125 acquires heartbeats of a subject P from an electrocardiograph (not shown). The interface 125 may acquire a blood beat of the subject P from a pulse meter (not shown). FIG. 2 is a flow chart showing an example of the procedure of the T1 map generation processing.

(TI Map Generation Processing)
(Step Sa1)

An interface 125 accepts a setting of a pulse relation in a T1 sequence from an operator. For example, the interface 125 accepts at least one of the range of a heart rate or the range of a pulse rate, a plurality of inversion times, and the number of inversion pulse times (hereinafter, referred to "the number of inversion times"). The interface 125 outputs the setting of the pulse relation to a processing circuitry 131.

Figure 3:
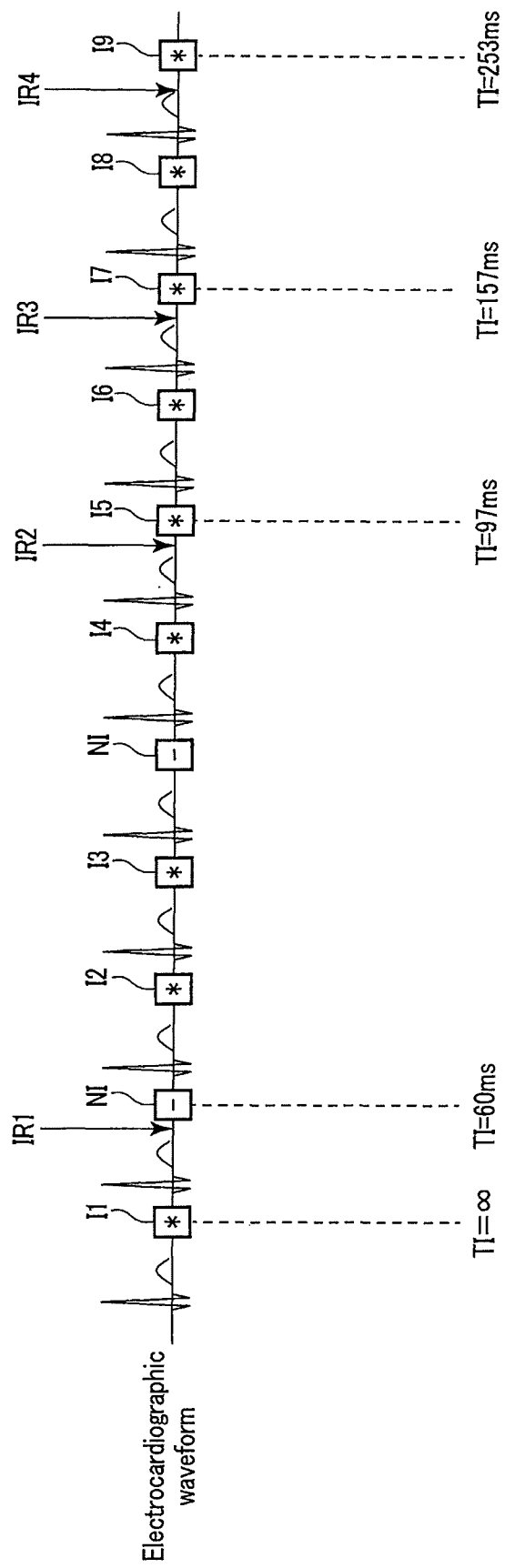
FIG. 3 is a view illustrating an example of a pulse relation in the embodiment along with the inversion time.

FIG. 3 is a view illustrating an example of a pulse relation along with inversion times. As illustrated in FIG. 3, the pulse relation includes pre-inversion imaging executed in a heartbeat prior to a first inversion pulse IR1, a plurality of non-read-out periods respectively corresponding to a plurality of heartbeats in which read-out of MR signals is not executed after the execution of the first inversion pulse IR1 (in other words, no RF pulse is applied to the subject P), and a plurality of unrelaxed IR pulses. In FIG. 3, a plurality of collection timings are each represented by a symbol "*". Specifically, the plurality of collection timings illustrated in FIG. 3 are nine timings of the first imaging I1 indicating pre-inversion imaging, the second imaging I2 in which an inversion time TI corresponds to 60 ms+an RR interval, the third imaging I3 in which the inversion time TI corresponds to 60 ms+2×an RR interval, the fourth imaging I4 in which the inversion time TI corresponds to 60 ms+4×an RR interval, the fifth imaging I5 in which the inversion time TI corresponds to 97 ms, the sixth imaging I6 in which the inversion time TI corresponds to 97 ms+an RR interval, the seventh imaging I7 in which the inversion time TI corresponds to 157 ms, the eighth imaging I8 in which the inversion time TI corresponds to 157 ms+an RR interval, and the ninth imaging I9 in which the inversion time TI corresponds to 253 ms.

As illustrated in FIG. 3, as an initial collection timing among the plurality of collection timings, MR signals are collected at the first imaging I1 before the first inversion pulse IR1 is applied to the subject P. FIG. 3, a non-read-out period is represented by a symbol "-". The non-read-out period shown in FIG. 3 is set at NI in the second heartbeat immediately after the first inversion pulse IR1 and at NI in the fifth heartbeat. A plurality of unrelaxed IR pulses in FIG. 3 correspond to a second inversion pulse IR2, a third inversion pulse IR3, and a fourth inversion pulse IR4. As illustrated in FIG. 3, the pulse relation in FIG. 3 is defined by four different invention times (TI=60 ms, TI=97 ms, TI=157 ms, and TI=253 ms), two non-read-out periods, and three unrelaxed IR pulses.

(Step Sa2)

The processing circuitry 131 selects one collection pattern from a plurality of collection patterns, based on the setting accepted by the T1 sequence determining function 1315 in Step Sa1. As an example of schematically showing a collection pattern, when an inversion pulse is represented by a symbol "/", a collection timing is represented by a symbol "*", and a non-read-out period is represented by a symbol "-", a collection pattern corresponding to FIG. 3 results in "*/-**-*///*". The processing circuitry 131 makes the selected collection pattern displayed as a setting screen of imaging conditions on a display 127. At this time, the processing circuitry 131 may cause the display 127 to display the setting accepted via the interface 125 along with the selected collection pattern.

FIG. 4 is a view illustrating an example of a plurality of T1 sequences respectably corresponding to a plurality of collection patterns. A storage apparatus 129 stores a correspondence list of the plurality of collection patterns relative to settings of a plurality of pulse relations. The plurality of collection patterns stored in the storage apparatus 129 are not limited to the collection patterns illustrated in FIG. 4.

For example, when TI=60 ms, TI=97 ms, TI=157 ms, and TI=253 ms are entered as a plurality of inversion times via the interface 125, the processing circuitry 131 selects a collection pattern indicating "*/-**-*///*" among the plurality of collection patterns shown in FIG. 4. In addition, when the range of a heart rate or the range of pulse rate corresponding to 50 to 75 bpm (beats per minute) and the number of inversion times of "3" are accepted as a pulse relation, the processing circuitry 31 selects a collection pattern indicating "*-/*-*-*-/-*/*" among the plurality of collection patterns by a T1 sequence determining function 1315.

The plurality of T1 sequences shown in FIG. respectively include a combination of pre-inversion imaging, a collection pattern having at least one of the three references (to be described later), and a plurality of inversion times. Hereinafter, the pre-inversion imaging and the three references will be described in detail.

(1) Pre-Inversion Imaging

In a calculation of T1 values using data collected by a MOLLI method, a parameter A indicating a signal value of an MR signal at the time of an infinite inversion time, i.e., at the time when the longitudinal magnetization completely recovers, and a parameter B' in which "1" is added to the efficiency of an inversion pulse (hereinafter, referred to as "inversion efficiency") are indirectly calculated. The parameter A is a relative signal value with reference to a signal value of an MR signal corresponding to the longitudinal magnetization in a thermal equilibrium state prior to the execution of the MOLLI method (hereinafter, referred to as "thermal equilibrium signal value"). Therefore, calculation errors in the parameter A and parameter B' calculated in the calculation process of a T1 value result in an error factor. For example, in the calculation process of a T1 value, the following factors have an influence on the value of the parameter A and the value of the parameter B'. The factors are a change in signal value due to the application of an RF pulse at the time of reading out an MR signal (hereinafter, referred to as "read-out change"), applying an invention pulse before the longitudinal magnetization completely recovers, and the inversion efficiency being not "1", Due to these factors, a systematic error occurs in the calculated T1 value. In order to correctly estimate the read-out change, an effective flip angle is required which corresponds to a pixel value of each of a plurality of pixels in a B1 map representing a distribution of transmission intensities of an RF pulse. To determine the effective flip angle, additional imaging, for example, a double angle method is required in addition to the MOLLI method, leading to a problem in which the imaging time is prolonged.

In contrast, according to the pre-inversion imaging in a T1 sequence in the present embodiment, it is possible to collect a signal value of an MR signal which is close to a signal value obtained when the longitudinal magnetization completely recovers. The signal values collected by pre-inversion imaging correspond to thermal equilibrium signal values. In addition, the signal values collected by the pre-inversion imaging may be used to determine the inversion efficiency, based on the relation with the signal values collected immediately after the next inversion pulse, for example, a comparison therebetween. Thereby, the accuracy of the estimation of the inversion efficiency is improved in the processing of Step Sa6 (to be described later) using thermal equilibrium signal values. Therefore, the accuracy of the estimation of a read-out change is improved even if a rough flip angle is used. Based on the matters described above, it is possible to drastically reduce the influence of a flip angle relative to a T1 value determined in the processing of Step Sa6 (to be described later). In other words, it is possible to calculate a T1 value with high accuracy by using, in the calculation of T1 values, signal values collected by pre-inversion imaging.

(2) First Reference

The relativity between a collection timing and a calculation of a T1 value will be described. In a physical process of the relaxation of the longitudinal magnetization, a signal value (also referred to as "signal intensity") of an MR signal consecutively recovers from a negative value after the application of an inversion pulse to a positive value toward a thermal equilibrium signal value, depending on a T1 value. For this reason, sign-attached signal values are used in calculation of T1 values. As the signal values, pixel values at the same position in a plurality of MR images respectively corresponding to a plurality of inversion times are used. Since the pixel values in MR images are represented by absolute values of signal values, a negative sign needs to be recovered for the signal values in the plurality of MR images at the prior step of the calculation of a T1 value.

A signal value provided with a sign (hereinafter, referred to as "sign-attached signal value") $F_1$ is generated by selecting signal values whose signs are inverted from a plurality of signal values (hereinafter, referred to as absolute values) $F_{Ni}$ respectively corresponding to a plurality of pixels at the same position of a plurality of MR images and inverting the sign of the selected signal values. Here, the subscript "i" is a positive integer (i=1, . . . , N) indicating the order of MR images generated by the execution of a T1 sequence. The subscript "N" is the total number of MR images generated by the execution of the T1 sequence. In a simple method, in the case where absolute values are arranged in the ascending order of invention times, a sign-attached signal value is generated by multiplying an absolute value in an MR image generated before Np corresponding to a specific "i" (i<Np) by −1 as shown in the cases described below.

$$F_i = -F_{Ni} \ (i<Np)$$

$$F_i = F_{Ni} \ (i \geq Np)$$

Figure 11:
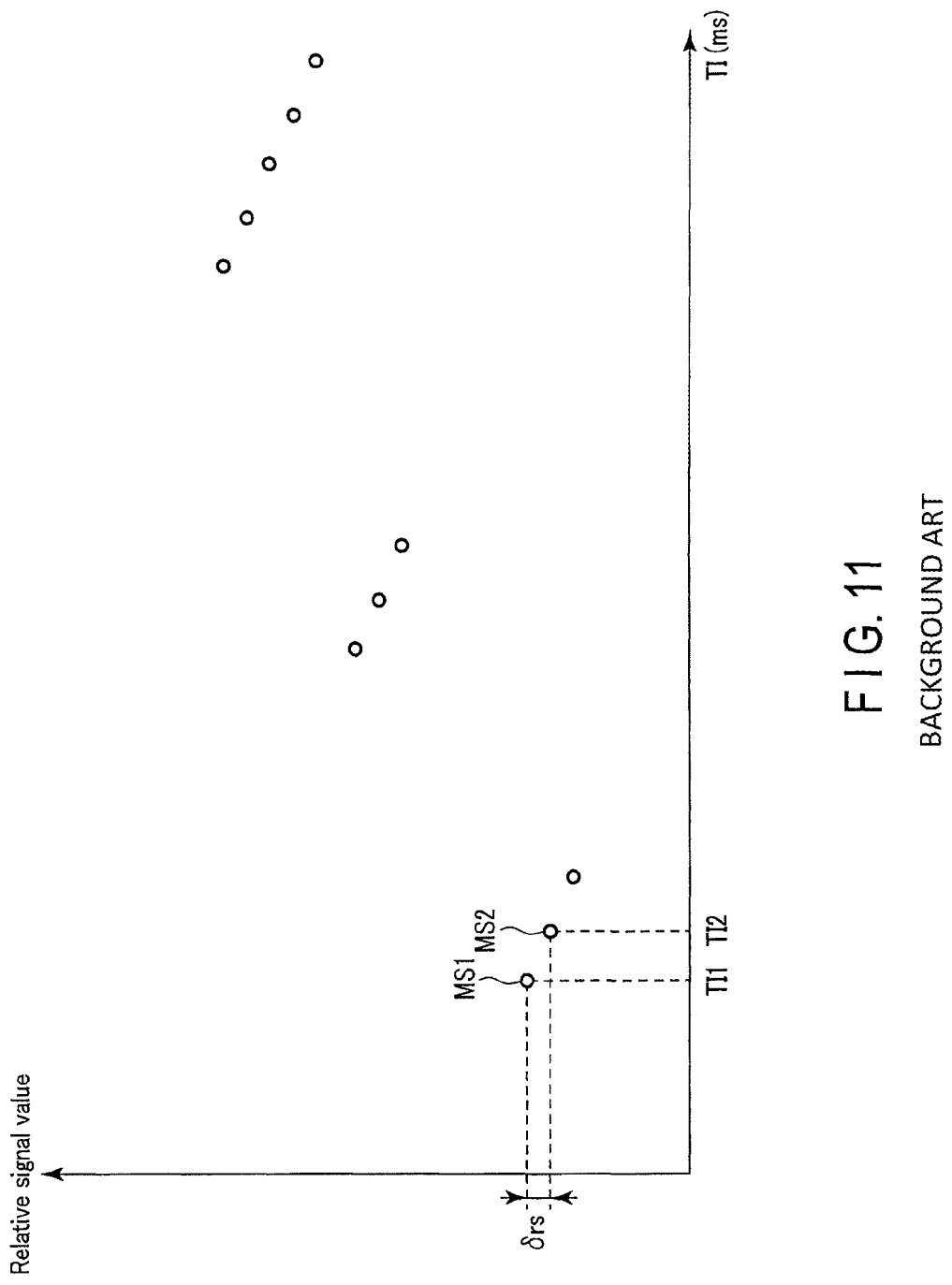
FIG. 11 is a view illustrating an example where data collected in a conventional MOLLI method is plotted as relative signal values against the TI (inversion times).

Since sign-attached signal values are generally arranged in the ascending order relative to the inversion times except for an influence of noise, sign-attached signal values can be generated by the above described method. However, there may be a case where depending on the intervals of the invention pulses and inversion times in a T1 sequence, the absolute values on or after Np are not arranged in the ascending order relative to the inversion times as illustrated in, for example, FIG. 11. In such a case, a T1 value is calculated using erroneously generated sign-attached signal values, and the calculated T1 value resultantly has a significant calculation error.

Based on the matters described above, as a first reference, the plurality of collection patterns in the T1 sequence are set such that the signal intensity of an MR signal is monotonously increased with the ascending order of the inversion time from the time point of applying an inversion pulse to the time point of each of the plurality of collection timings. Furthermore, since a non-read-out period can be set discretionally in accordance with the first reference after an inversion pulse "/" as shown by the symbol "-" in the collection patterns in FIG. 4, the sign can be recovered such that the sign-attached signal value can be monotonously increased along the ascending order of the inversion time, making it possible to improve the calculation accuracy of T1 values. It should be noted that in a non-read-out period, a gradient magnetic field may be applied similarly to the case of collecting an MR signal. At this time, since the influence of the eddy from the gradient magnetic field in a receive coil can be kept in the same manner as in the case of imaging, the pattern of generated sounds during the imaging can be made homogeneous over the execution period of the T1 sequence. With this configuration, it is possible to reduce a psychological burden to a subject P in the execution period of the T1 sequence.

Hereinafter, an example of the procedure for determining collection timings relating to the first reference will be described. The collection timings may be determined at the processing circuitry 131 or may be preliminarily determined, for example, by an apparatus different from the MRI apparatus 1, for example, a work station.

A plurality of signal intensities accompanied by signs to be collected in a certain collection pattern are estimated using a simulation, etc. in each of a plurality of inversion times. Next, a drop width of a signal intensity can be calculated by determining a difference, from an estimated value of a signal intensity in a certain inversion time among a plurality of inversion times, a signal value corresponding to an inversion time longer than this inversion time. A maximum value of the calculated drop widths (hereinafter, referred to as "maximum drop width") is specified for each of the plurality of invention times. In a non-read-out period in a collection pattern relating to the estimation of a signal intensity, a signal intensity which is estimated when a signal is tentatively collected (hereinafter, referred to as "tentative estimation value") is calculated in the same manner as in the above described procedure. A maximum value (hereinafter, referred to as "tentative maximum drop width") is specified by using the tentative estimation value in the same manner as in the above described procedure. A plurality of collection timings are determined such that the maximum drop width is smaller than all tentative maximum drop widths or the maximum drop width is equal to or less than 0.

Figure 5:
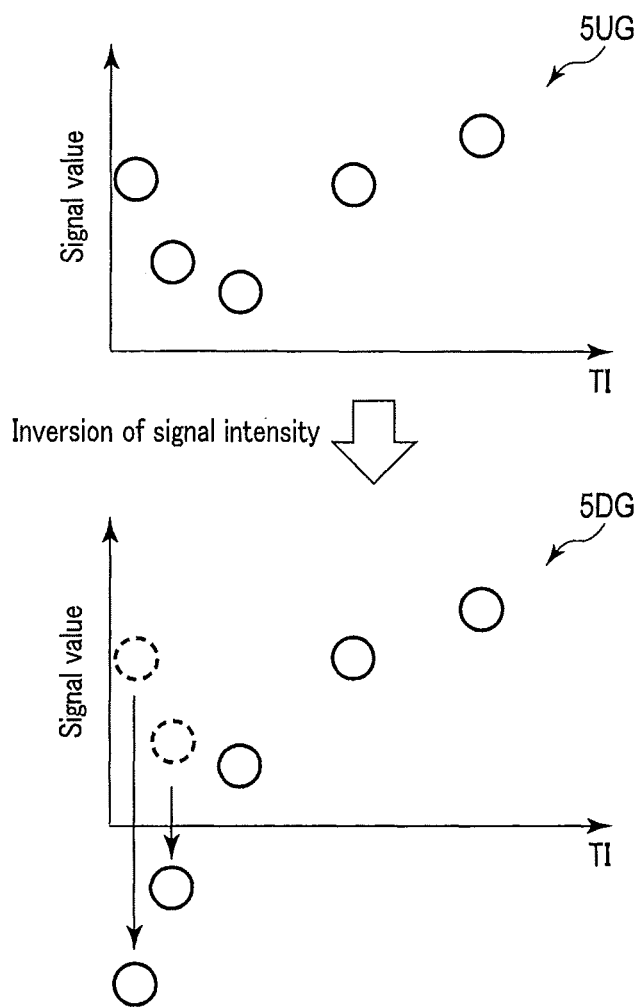
FIG. 5 is a view illustrating an example of recovery of signs of signal values in the embodiment.

When the T1 sequence MI1 shown in FIG. 4 is executed on a subject P with a low heart rate, the sign-attached signal values are in the ascending order in most cases. FIG. 5 is a view illustrating an example of a recovery of signs of signal values. The horizontal axes in the graphs illustrated in FIG. 5 indicate the inversion time (TI). The vertical axes of the graphs in FIG. 5 indicate signal values (pixel value) of pixels in MR images. The upper graph 5UG in FIG. 5 shows a distribution of signal values of the same pixel in a plurality of MR images generated based on the MR signal collected in each of the plurality of inversion times relative to a plurality of inversion times. Since the pixel values in the MR images are represented by absolute values, all signal values are positive as shown in the upper graph 5UG.

The lower graph 5DG in FIG. 5 is a view showing an example in which the two signal values in inversion times shorter than the invention time with the smallest signal value in the graph 5UG are symmetrically inverted relative to the horizontal axis. As illustrated in the lower graph 5DG in FIG. 5, a plurality of sign-attached signal values monotonously increase with an increase in the inversion time, in other words, in the ascending order in line with the ascending order of the invention time, and it is possible to calculate a T1 value with high accuracy. That is, the calculation errors in T1 values can be reduced by the execution of a T1 sequence based on the first reference.

(3) Second Reference

In FIG. 4, the T1 sequence MI2 in which the range of a heart rate is wide, and the number of inversion times is 4 has a non-read-out period in the fourth heartbeat after application of the first inversion pulse. The collection pattern of the T1 sequence MI2 is "*/-**-*///*" as shown in FIG. 3. The inversion times in the T1 sequence MI2 are 60, 97, 157, and 253 in the ascending order. If a read-out, i.e., a collection of an MR signal is performed in the fourth heartbeat NI after application of the first inversion pulse IR1, the intervals of read-out in the case of a high heart rate shorten, and thus the calculation error concerning a large T1 value increases. For this reason, when imaging is performed in consecutive heartbeats, it is necessary to incorporate a heartbeat in which imaging is stopped, i.e., a non-read-out period, into a pulse sequence to calculate a large T1 value with high accuracy.

FIG. 6 is a view illustrating an example of relative errors of T1 values when the T1 sequence MI2 using a flip angle 10° or 13° is executed relative to different heart rates. As illustrated in FIG. 6, in the case of a collection pattern of "*/-**-*///*", the relative errors of the calculated T1 values are small values of 2% or less, regardless of the heart rate and the flip angle.

FIG. 7 is a view illustrating, as a comparative example, an example of relative errors of T1 values when a pulse sequence having the same inversion times as those of the T1 sequence MI2, a flip angle of 10° or 13°, and a collection pattern of "*/-**//**/*" is executed relative to different heart rates. As illustrated in FIG. 7, in the case of a collection pattern of "*/-**//**/*", the calculated relative errors of T1 values increase with an increase in the heart rate and an increase in the flip angle as compared with the relative errors of T1 values shown in FIG. 6.

From the above matters, it turned out that when imaging is executed over four or more heartbeats after one time inversion pulse, by stopping read-out i.e., providing a non-read-out period, in the second heartbeat or the third heartbeat, the calculation accuracy of T1 values tends to be improved. If such a non-read-out period is incorporated in a collection pattern, imaging may be performed in the second heartbeat or the third heartbeat after another inversion pulse.

Based on the foregoing, as a second reference, when imaging is executed over three or more heart beats or three or more blood beats following the application of an inversion pulse, a T1 sequence includes a non-read-out period in which MR data is not collected in at least one heartbeat or at least one blood beat of a plurality of heartbeats or a plurality of blood beats included between a time point of application of an inversion pulse and a time point of application of the next inversion pulse executed after the application of the invention pulse. That is, a T1 sequence relating to the second reference includes one or more non-read-out periods during a plurality of heart beats respectively corresponding to a plurality of collections by using an imaging-related inversion pulse in a collection pattern including an inversion pulse (hereinafter, referred to as "imaging-related inversion pulse") relating to a plurality of collections over three or more heart beats after a certain inversion pulse. That is, the second reference is that read-out is not performed in one heartbeat anywhere in a plurality of heartbeats relating to a plurality of collections relating to the imaging-related inversion pulse.

(4) Third Reference

The T1 sequence MI2 in FIG. 4 includes a non-read-out period immediately after the first inversion pulse IR1 as illustrated in FIG. 3. FIG. 8 is a view illustrating, as a comparative example, an example of relative errors of T1 values in the case of executing a pulse sequence having the same inversion times as the inversion times in the T1 sequence MI2, a flip angle of 10° or 13°, and a collection pattern of "*/***-*///*" relative to different heart rates. As shown in FIG. 8, in the case of a collection pattern of "*/***//**/*", the calculated relative errors of T1 values increase as the flip angle is increased and the heart rate lowers as compared with the relative errors of T1 values shown in FIG. 6. That is, as illustrated in FIG. 8, the calculation accuracy of a large T1 value when the heart rate is low degrades as compared with the calculation accuracy shown in FIG. 6. Such a degradation in calculation accuracy tends to occur when the inversion time is short. This phenomenon can be avoided, for the imaging to be performed when the inversion time is short, by not collecting an MR signal immediately after an inversion pulse or not collecting an MR signal immediately before an inversion pulse.

When performing an inversion pulse immediately after a decrease in signal value due to read-out of an MR signal, i.e., a collection of an MR signal and then performing imaging in a short inversion time again, the collection interval of the MR signal shortens. For this reason, in the case of a large T1 value, a signal value collected after the inversion pulse becomes smaller. Therefore, in such imaging using a large T1 value, new information (signal value) to be used for calculation of a T1 value cannot be obtained in the second imaging. From these matters, in order to measure a large T1 value with high accuracy, a collection pattern is preferred which includes non-read-out periods consecutively crossing over an inversion pulse.

From the matters described above, as a third reference, a T1 sequence includes a non-read-out period in which no MR data is collected in a heartbeat or a blood beat immediately before an inversion pulse or in a heartbeat or a blood beat immediately after an inversion pulse. It should be noted that as the third reference, in a T1 sequence, an inversion pulse may be applied to a subject P at short intervals, for example, at intervals of five or less heartbeats or five or less blood beats, in addition to the above described contents.

By using the third reference, a collection pattern having short inversion times can be set in such a manner that an inversion pulse is applied before the longitudinal magnetization completely recovers. It is possible to obtain the same information (signal values) as in the case of collecting an MR signal in an inversion time corresponding to the time interval of two collections of MR signals immediately after the inversion pulse by executing the inversion pulse before the longitudinal magnetization completely recovers. In a common collection method, such as a MOLLI method in which an MR signal is collected after waiting for recovery of the longitudinal magnetization, a collection of an MR signal in a long inversion time is required to collect a T1 value with high accuracy. In contrast, when an inversion pulse is applied before the longitudinal magnetization completely recovers like the collection patterns according to the embodiment, a large T1 value can be calculated with high accuracy even if an inversion time relating to the execution of collection is short.

(Step Sa3)

When an instruction for changing a setting of the pulse relation is entered via the interface 125, the processing circuitry 131 repeats the processing of Step Sa1 and the processing of Sat by the T1 sequence determining function 315 (Step Sa3: "Yes"). When an instruction for determining the setting of the pulse relation is entered via the interface 125, the processing circuitry 131 determines a T1 sequence using the selected collection pattern and the accepted setting. It should be noted that the processing circuitry 131 may automatically determine a T1 sequence based on imaging conditions including the heart rate of a subject, presence or absence of use of an imaging agent, the frequency of heartbeat fluctuation, and the like.

For example, if as a setting accepted at Step Sa1, TI=60 ms, TI=170 ms, and TI=482 ms are entered via the interface 125 and a collection pattern indicating "*-/*-*-*-/-*/*" is selected, the processing circuitry 131 determines a T1 sequence as shown below responsive to an entry of the instruction for determining a T1 sequence.

Collection Pattern: *-/*-*-*-/-*/*

Value of Inversion Time (TI)

TI in the first imaging before the first inversion pulse: 482 ms (corresponding to TI=∞)

TI in the second imaging after the first inversion pulse: 482 ms

TI in the third imaging after the second imaging: (482+2×RR interval) ms

TI in the fourth imaging after the third imaging: (482+4×RR interval) ms

TI in the fifth imaging after the second inversion pulse: (170+RR interval) ms

TI in the sixth imaging after the third inversion pulse: 60 ms

The processing circuitry 131 outputs the determined T1 sequence to a sequence control circuitry 121. An FFE (Fast Field Echo) sequence having a spoiler pulse that erases transverse magnetization before reading out an MR signal, i.e., a spoiled gradient echo method, is used as an imaging method in the T1 sequence. A gradient spoiler or an RF spoiler is used as the spoiler pulse. Hereinafter, the embodiment will be described assuming that a T1 sequence having a collection pattern indicating "*-/*-*-*-/-*/*" is executed by the sequence control circuitry 121.

(Step Sa4)

The sequence control circuitry 121 executes imaging over the subject P in synchronization with the heartbeats (electrocardiogram (ECG) gated) or in synchronization with blood beats in accordance with the T1 sequence using the selected collection pattern and the accepted setting. The processing circuitry 131 collects an MR signal corresponding to each of the plurality of inversion times.

(Step Sa5)

The processing circuitry 131 generates an MR image corresponding to each of the plurality of inversion times using the collected MR signal by an image generation function 1313. The generated MR image is made to correspond to the inversion time and stored in a storage apparatus 129. The pixel value of each of a plurality of pixels in the MR images corresponds to a signal intensity that reflects the magnitude of the longitudinal magnetization at a position corresponding to a pixel.

(Step Sa6)

The processing circuitry 131 determines a T1 value by using the imaging conditions in the T1 sequence and a model simulating a change in the longitudinal magnetization using T1 values as parameters by a T1 map generation function 1317 so that a difference between a signal value corresponding to each of the plurality of inversion times and a pixel value in each of the plurality of MR images becomes minimum. With this configuration, the processing circuitry 131 executes determination of a T1 value in the MR images on a pixel to pixel basis.

Specifically, the processing circuitry 131 determines such a T1 value that minimizes a value of an objective function using a T1 value as a variable (unknown number) in the optimization on a pixel to pixel basis, by the T1 map generation function 1317 by using various optimization methods, such as a golden section method. The objective function has three main parameters: a thermal equilibrium signal value A, an inversion efficiency B, and a T1 value. As explained later, since the thermal equilibrium signal value A and the inversion efficiency B can be calculated from a calculated T1 value, the parameter in the objective function substantially becomes one variable of a T1 value. Hereinafter, the objective function will be described, and then a model will be described.

A signal value $f_i$ of an MR signal is represented by the following equation (1) by using a pixel-by-pixel relative signal value $g_i$ which is calculated by a simple simulation using a model.

$$f_i(T_1) = A g_i(T_1, t_1, \ldots, t_i, \ldots, t_N, T_{IR1}, \ldots, T_{IRi}, \ldots T_{IRN}, B) \quad (1)$$

In the equation (1), $g_i$ is a pixel-by-pixel relative signal value calculated by a simple simulation using a model at the time point of collecting an $i^{th}$ MR image (a signal value obtained when a signal value when imaging is performed in a state where the longitudinal magnetization is completely relaxed is normalized to "1"), $t_1$ is an inversion time at the time point of collecting the $i^{th}$ MR image, and $T_{IRi}$ is, when an inversion pulse is applied before the collection of the $i^{th}$ MR image, a time interval between this inversion pulse and the next inversion pulse. It is assumed that when collecting an MR image involving no inversion pulse, $T_{IRi}$ is zero (=0).

Summarizing the equation (1) as a column vector relative to (i=1, . . . , N), the result is represented as the following equation (2).

$$f(T_1) = A g(T_1, t_1, \ldots, t_i, \ldots, t_N, T_{IR1}, \ldots, T_{IRi}, \ldots T_{IRN}, B) \quad (2)$$

Assuming that the inversion efficiency B changes to a line shape between 1.0 and 0.9, the equation (1) is represented as follows, using variables c and d.

$$f_i(T_1, t_1, \ldots, t_i, \ldots, t_N, T_{IR1}, \ldots, T_{IRi}, \ldots T_{IRN}, B) =$$
$$A\{bg_i(T_1, t_1, \ldots, t_i, \ldots, t_N, T_{IR1}, \ldots, T_{IRi}, \ldots T_{IRN}, 0.9) +$$
$$(1-b)g_i(T_1, t_1, \ldots, t_i, \ldots, t_N, T_{IR1}, \ldots, T_{IRi}, \ldots T_{IRN}, 1.0)\} =$$
$$cg_i(T_1, t_1, \ldots, t_i, \ldots, t_N, T_{IR1}, \ldots, T_{IRi}, \ldots T_{IRN}, 0.9) +$$
$$dg_i(T_1, t_1, \ldots, t_i, \ldots, t_N, T_{IR1}, \ldots, T_{IRi}, \ldots T_{IRN}, 1.0)$$

In the above equation, c=Ab, d=A(1−b)=A−Ab=A−c. The variable b and the inversion efficiency B have such a linear relation that when b=0, B=1.0, and when b=1, B=0.9, and thus B is represented by 1.0−0.1b (B=1.0−0.1b). In addition, d=A−c=c/b−c, and thus b=c/(c+d). Therefore, A=c+d, B=1.0−0.1c/(c+d). Furthermore, c and d are represented by c=10A−10AB, and d=A−c=−9A+10AB. Herein, if $p_i$ and $q_i$ are represented by the following equations, $$p_i = (g_i)(T_1, t_1, \ldots, t_i, \ldots, t_N, T_{IR1}, \ldots, T_{IRi}, \ldots T_{IRN}, 0.9)$$

$$q_i = g_i(T_1, t_1, \ldots, t_i, \ldots, t_N, T_{IR1}, \ldots, T_{IRi}, \ldots T_{IRN}, 1.0)$$

and summarizing $p_i$ and $q_i$ as a column vector across (i=1, N), the equation (2) is represented by the following equation (3).

$$f(T_1) = cp + dp = (10A - 10AB)p + (-9A + 10AB)q \quad (3)$$

When the equation (3) is transformed, the following equation (4) is obtained.

$$\frac{f(T_1)}{A} = (10 - 10B)p + (-9 + 10B)q = 10p - 9q + B(10q - 10p) \quad (4)$$

When the equation (4) is transformed by adding the following term in which a representative value $B_{fix}$ of the inversion efficiency is used in both sides of the equation (4), $$B_{fix}(10q - 10p)$$

the following result is obtained.

$$\frac{f(T_1)}{A} - B_{fix}(10q - 10p) = \quad (5)$$
$$10p - 9q + (B - B_{fix})(10q - 10p)10p - 10q + B_{fix}(10q - 10p) =$$
$$\frac{f(T_1)}{A} - (B - B_{fix})(10p - 10q)(10 - 10B_{fix})p + (10B_{fix} - 9)q =$$
$$(f(T_1)10(p - q))\begin{pmatrix} 1/A \\ B - B_{fix} \end{pmatrix} \equiv H\begin{pmatrix} 1/A \\ B - B_{fix} \end{pmatrix}$$

When a pixel value of an MR image generated by the execution of a T1 sequence is represented by $F_i$, a matrix H in the equation (5) is represented as follows by using a column vector (hereinafter, referred to as "measured vector") F in which $F_i$ is arranged in the form of a column, $H=(F10(p-q))$.

Estimated values of the parameters in the equation (5) are represented by the following equation (6), based on a linear optimization formula.

$$v_1(T_1) \equiv \frac{1}{A} \quad (6)$$

$$v_2(T_1) \equiv B - B_{fix}$$

$$\begin{pmatrix} v_1(T_1) \\ v_2(T_1) \end{pmatrix} \cong$$

$$(H^T H + N \cdot \lambda_B^2 \cdot WW^T)^{-1} H^T ((10 - 10B_{fix})p + (10B_{fix} - 9)q)$$

$$W = \begin{pmatrix} 0 & 0 \\ 0 & 1 \end{pmatrix}$$

Where $\lambda_B^2$ is a normalization parameter. The parameters $v_1(T_1)$ and $v_2(T_2)$ obtained by the equation (6) are obtained by minimizing the following equation (7).

$$\frac{1}{N}s^2 \equiv \frac{1}{N} \left| (10 - 10B_{fix})p + (10B_{fix} - 9)q - H \begin{pmatrix} v_1(T_1) \\ v_2(T_1) \end{pmatrix} \right|^2 + w(B, B_{fix}) \quad (7)$$

The w in the equation (7) is defined by the following equation.

$$w(B, B_{fix}) \equiv \lambda_B^2 (B - B_{fix})^2 = \lambda_B^2 \cdot \left| W \begin{pmatrix} v_1(T_1) \\ v_2(T_1) \end{pmatrix} \right|^2$$

If both sides of the equation (7) are multiplied by $A^2$ to set the dimension in the equation (7) to a square of a signal value, the following equation is obtained.

$$\frac{s^2 A^2}{N} \equiv \frac{A^2}{N} \left| (10 - 10B_{fix})p + (10B_{fix} - 9)q - H \begin{pmatrix} v_1(T_1) \\ v_2(T_1) \end{pmatrix} \right|^2 + A^2 \lambda_B^2 \cdot \left| W \begin{pmatrix} v_1(T_1) \\ v_2(T_1) \end{pmatrix} \right|^2 \quad (8)$$

The right-hand side of the equation (8) is a function of only a T1 value. Therefore, the processing circuitry 131 can calculate an estimated value of T1, $$\tilde{T}_1$$

by calculating such a T1 value that minimizes the right-hand side of the equation (8) by the T1 map generation function 1317. When the estimated value of the T1 value is obtained, the processing circuitry 131 can determine estimated values $$\tilde{A}, \tilde{B}$$

of the thermal equilibrium signal value A and the inversion efficiency B from the following calculations $$\tilde{A} = v_1(\tilde{T}_1)$$

$$\tilde{B}_2 = v_2(\tilde{T}_1) - B_{fix}$$

by the T1 map generation function 1317. A resulting signal value obtained by applying a relative signal value $g_i$, which is a result of a simple simulation using a model, to the equation (3), $$f(\tilde{T}_1)$$

is represented as follows.

$$f(\tilde{T}_1) = cp + dp = \tilde{A}g(T_1, t_1, \ldots, t_i, \ldots, t_N, T_{IR1}, \ldots, T_{IRi}, \ldots T_{IRN}, \tilde{B})$$

By using a difference between a measured vector and a signal value as a simulation result, and a penalty term, $$F - f(\tilde{T}_1)$$

an objective function s' is defined by the following equation (9).

$$s' \equiv |F - \tilde{A}g(T_1, t_1, \ldots, t_i, \ldots, t_N, T_{IR1}, \ldots, T_{IRi}, \ldots T_{IRN}, \tilde{B})|^2 \lambda_B^2 \tilde{A}^2 (B_{fix} - \tilde{B})^2 \quad (9)$$

The processing circuitry 131 executes the calculation of a T1 value using the equation (9) by the T1 map generation function 1317. In the equation (9), the value of a normalization parameter λB in the penalty term is, for example, 0.05, and the value of a representative value $B_{fix}$ of the inversion efficiency is, for example, 0.93. If a large value, such as 1, is used as the normalization parameter λB, the parameter B is fixed to approximately the value of $B_{fix}$, and the processing circuitry 131 can perform the estimation with two variables (thermal equilibrium signal value A and a T1 value). At this time, in the calculation of a T1 value, system errors caused by using the value of B increase; however, the stability against noise is improved. It should be noted that the thermal equilibrium signal value A is generally determined by a signal value of an MR signal collected in pre-inversion imaging, and thus the only completely free parameter in the objective function s' is the value T1.

Hereinafter, the simple simulation based on a model used for the calculation of a relative signal value $g_i$ will be described. If Steady-State Free Precession (SSFP) is used as imaging in a T1 sequence, the behavior of spins included in one pixel or one voxel becomes complicated. For this reason, a complicated calculation is required to accurately determine what signal value is to be measured. However, if a spoiled gradient echo method is used in a T1 sequence, a spoiler pulse which erases transverse magnetization before application of the next RF pulse after reading out an MR signal following application of an RF pulse is applied, and thus the transverse magnetization becomes zero. Therefore, the processing circuitry 131 can calculate, in the T1 map generation function 1317, a signal value of an MR signal for each inversion time by a comparatively simple calculation. In the calculation of signal values of MR signals over an execution period of a T1 sequence, a plurality of parameters as shown below are necessary.

T1 sequence (Collection pattern and collection timing (a value of the inversion time during imaging relating to each of a plurality of inversion pulses))

Time interval of the adjacent inversion pulse in a plurality of inversion pulses Trigger interval of heartbeats When executing the T1 sequence, an R wave is used as a trigger in the electrocardiographic waveform. Usually, the interval of an R wave is not constant; however, assuming that the rhythm of the R wave is constant, the processing circuitry 131 can determine the trigger interval from the heart rate of a subject P by the T1 map generation function 1317.

Echo time (TE)
Repetition time (TR)
Flip angle: (FA)
The number of phase encoding steps
Inversion efficiency B
T1 value (which is a parameter intended for imaging and an initial value at the time of a simulation)

In this simulation, as illustrated in FIGS. 3 and 4, it is assumed that the interval between collection timings, the interval between non-read-out periods, and the interval between a collection timing and a non-read-out period are equal to the trigger interval.

As an imaging sequence in this simulation, an FFE (spoiled gradient echo) involving a spoiler pule is assumed as an example. Herein, it is assumed that the transverse magnetization has been completely erased after the application of the spoiler pulse. In addition, it is assumed that as for a sequence concerning read-out of MR signals during a series of imaging in the T1 sequence, the same sequence is used. The sequence concerning read-out of MR signals is, for example, a scan sequence concerning arrangement of MR data in the k-space, for example, a centric order method. The estimated accuracy of the inversion efficiency B is improved by using a pixel value of an MR image obtained by the centric order method in the objective function of the equation (9), because the center of the k-space most highly contributes to the contrast of an MR image. It should be noted that the sequence concerning the read-out of MR signals is not limited to the centric order method, and other scan sequence, such as a sequential order method, and radial scanning may be used. The pixel value of the MR image obtained based on the above assumption by the execution of the T1 sequence is proportional to the pixel value of longitudinal magnetization. Hereinafter, a signal value of an MR signal in a steady state (at an infinite distance clock time), i.e., a thermal equilibrium signal value is regarded as "1", and the magnitude of a signal value is represented as a relative value (relative signal value). The following are descriptions on a model of various changes in signal value (hereinafter, referred to as "signal changes") in this simulation.

(1) Attenuation of Longitudinal Magnetization Depending on T1 Value

When a signal value "s" at a certain clock time is zero (0), a signal "s(t)" after an elapse of time by only time "t" from a certain clock time is represented by the following equation.

$$s(t)=1-(1-s(0))\exp(-t/T_1) \quad (10)$$

(2) Attenuation of Signal Due to Stabilization Pulse

The term "stabilization pulses" means a plurality of RF pulses which are applied to a subject P per imaging for stabilization of an MR signal immediately before applying the initial RF pulse during imaging. That is, the stabilization pulse is applied to a subject P before the application of an RF pulse in each of a plurality of collections in a T1 sequence. It is assumed that the number of application times $N_d$ of the stabilization pulse used in one imaging is fixed over a plurality of collections in the T1 sequence. It should be noted that if the stabilization pulse is not executed at the time point of the collection of an MR signal, the estimation of signal attenuation explained in this item is unnecessary.

As described above, the processing circuitry 131 executes a calculation by the T1 map generation function 1317, regarding a signal value at an infinite distance clock time as "1" in this simulation. When a result of the simulation by the processing circuitry 131 is applied to the equation (9) of the objective function, from the viewpoint of the consistency with a measured value, it is convenient to normalize a signal value measured when tentatively measuring an MR signal at an infinite distance clock time to "1". For this reason, the processing circuitry 131 multiplies a signal value calculated in the simulation in each of the collections of an MR signal (hereinafter, referred to as "a simulation calculation value") by a ratio $1/S_{Nd}$, which is a ratio of a thermal equilibrium signal value 1 obtained at an infinite distance clock time to a signal value when tentatively calculated at the infinite distance clock time. A multiplication value s" resulting from the simulation calculation value and the ratio is represented as $S''=S_c/S_{Nd}$ by using a simulation calculation value $S_c$ and the above described ratio. If a signal value before the application of the stabilization pulse is represented as $S_j$, the signal value results in $S_j \times \cos(\alpha)$ due to attenuation of the longitudinal magnetization with use of a flip angle $\alpha$. Thereafter, after an elapse of a repetition time TR, the stabilization pulse is applied again. On the other hand, a signal change during the repetitive time TR is as follows.

$$s(T_R)=1-(1-s(0))\exp(-T_R/T_1) \quad (11)$$

Therefore, the signal change from a time point immediately following the application of the stabilization pulse to the repetitive time $T_R$ is represented as follows.

$$s_{j+1}=1-(1-s_j\cos(\alpha))\exp(-T_R/T_1) \quad (12)$$

The signal change represented by equation (12) is repeated over the number of application times "$N_d$" of the stabilization pulse in one imaging. Therefore, if a signal value is measured tentatively at an infinite distance time clock, a signal value $S_{Nd}$ after the application of the stabilization pulse over the $N_d$ times can be obtained by repetitively calculating the equation (12) with a setting of $s_j=S_0=1$ over the $N_d$ times. It should be noted that the signal value after the application of the stabilization pulse over the $N_d$ times may be calculated according to the number of application times of the stabilization pulse, the repetitive time, and the flip angle by the processing circuitry 131, or may be stored in the storage apparatus 129 in the form of a correspondence list according to the number of application times of the stabilization pulse, the repetitive time, and the flip angle.

(3) Signal Change Due to Inversion Pulse

Due to an inversion pulse, the longitudinal magnetization is multiplied by −B by using the inversion efficiency B.

A signal change in a read-out period of an MR signal involving application of an RF pulse is identical to the equation (12) representing a signal change in the application period of the stabilization pulse. Therefore, assuming that $s_0$ in the case of j=0 in the equation (12) is a signal value before reading out an MR signal, when the number of steps of the phase encode is 60, a signal value immediately after the read-out, i.e., a signal value after the end of one imaging is $s_{60}$. At this time, the equation (12) represents a recurrence formula relating to $s_j$, and thus in order to calculate $s_{60}$, the equation (2) needs to be recursively calculated over 60 times. In order to speed up the calculation at the processing circuitry 131, $s_{60}$ may be calculated using, for example, the approximate equation f(x) described below.

$$f(x) = C\exp(-\kappa x) + D \quad (13)$$
$$\kappa \equiv \frac{1}{T_1} + \frac{-\log(\cos(\alpha))}{T_R}$$
$$D \equiv \frac{1}{\kappa T_1}$$
$$C = s_0 - D$$

An f(x) in the equation (13) is a signal value after a time x when a signal value so before the read-out is represented by f(0) and a flip angle is represented by $\alpha$. It should be noted that the equation (13) may be used for the calculation of attenuation of a signal due to the stabilization pulse. If SSFP is used as imaging in a T1 sequence, a relative signal value $g_i$ is calculated by changing the model in accordance with the change in the longitudinal magnetization in the SSFP.

Summarizing the processing of this step Sa6, the processing circuitry 131 calculates, by the T1 map generation function 1317, signal values of MR signals in a plurality of collection timings, based on a model for calculating a change in longitudinal magnetization in a relaxation process of the longitudinal magnetization, a change in longitudinal magnetization due to an inversion pulse, a change in longitudinal magnetization due to an RF pulse used for collections of MR signals, and a change in longitudinal magnetization due to a stabilization pulse applied to a subject for stabilization of an MR signal immediately before the application of the RF pulse. Next, the processing circuitry 131 calculates a T1 value such that the calculated signal values are matched with pixel values in a plurality of MR images generated based on the collected MR signals in the plurality of collection timings. Specifically, the processing circuitry 131 calculates a signal value on a pixel to pixel basis by an execution of a T1 sequence by using the equation (10), the equation (13), and the signal change due to an inversion pulse, piecewise.

More specifically, the processing circuitry 131 sectionalizes timewise the process of signal change during the execution period of a T1 sequence, by the T1 map generation function 1317, in accordance with (1) attenuation of the longitudinal magnetization depending on a T1 value, (2) attenuation of a signal due to a stabilization pulse, (3) a signal change due to an inversion pulse, and (4) a signal change due to read-out of an MR signal, based on imaging parameters relating to the execution of the T1 sequence and a collection pattern in the T1 sequence. Next, the processing circuitry 131 calculates a change in the longitudinal magnetization in each of the sectionalized ranges, using the equation (10) and the equation (13), and the like. Thereby, the processing circuitry 131 calculates a signal value varying timewise over the execution period of the T1 sequence. Next, the processing circuitry 131 determines a T1 value in which a corresponding pixel value (or a sign-attached signal value, or a value obtained by normalizing a sign-attached signal by a thermal equilibrium signal value) in each of the plurality of inversion times is consistent with the calculated signal value in each of the plurality of inversion times by comparing the corresponding pixel value with the calculated signal value. That is, the processing circuitry 131 determines a T1 value such that a value of the objective function s' (hereinafter, referred to as "function value") becomes a minimum.

Figure 9:
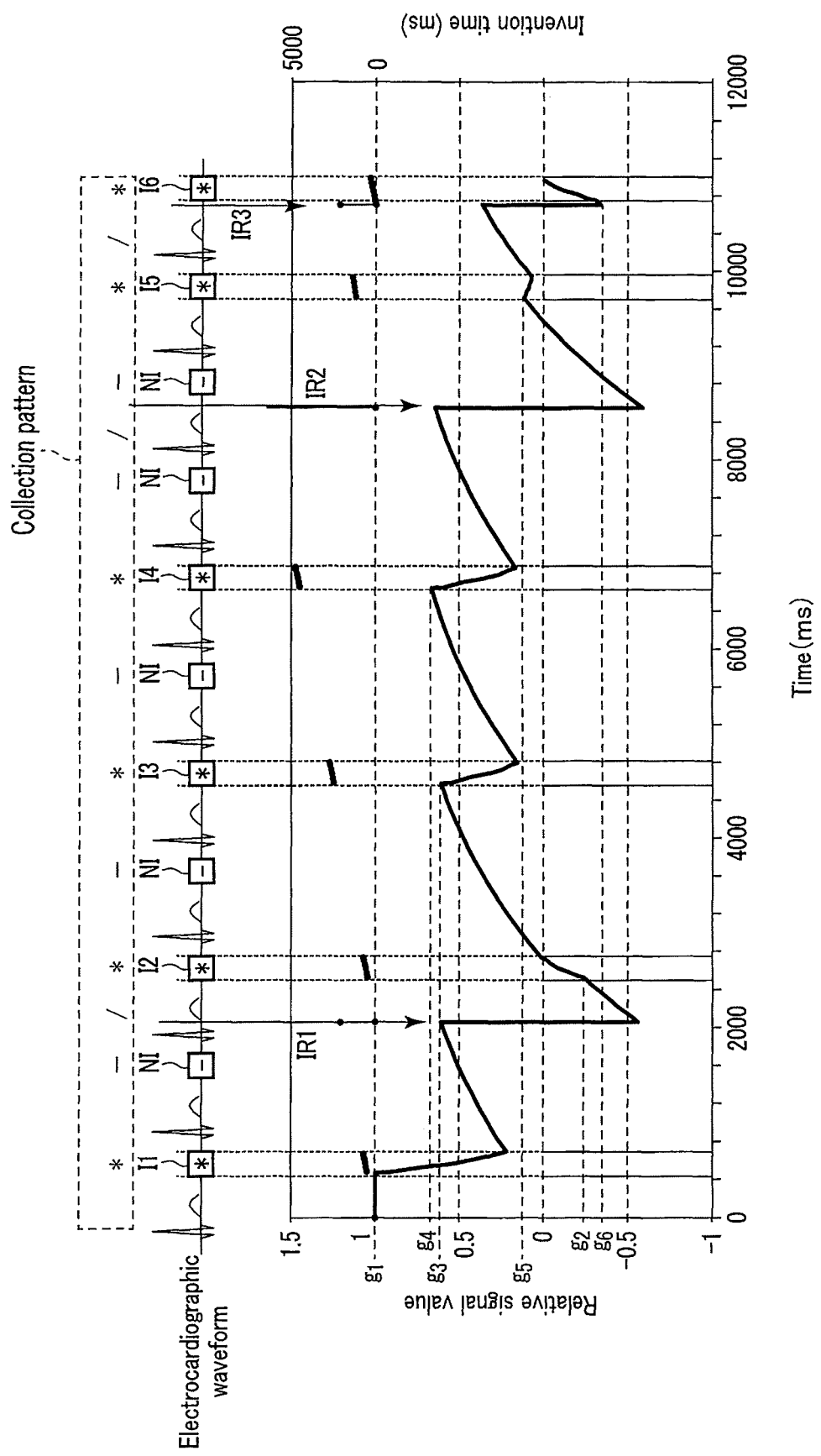
FIG. 9 is a view illustrating an example of calculation results of relative signal values in a certain pixel relating to a T1 sequence in the case where the collection pattern is "*-/*-*-*-/-*/*" in the embodiment.
Figure 10:
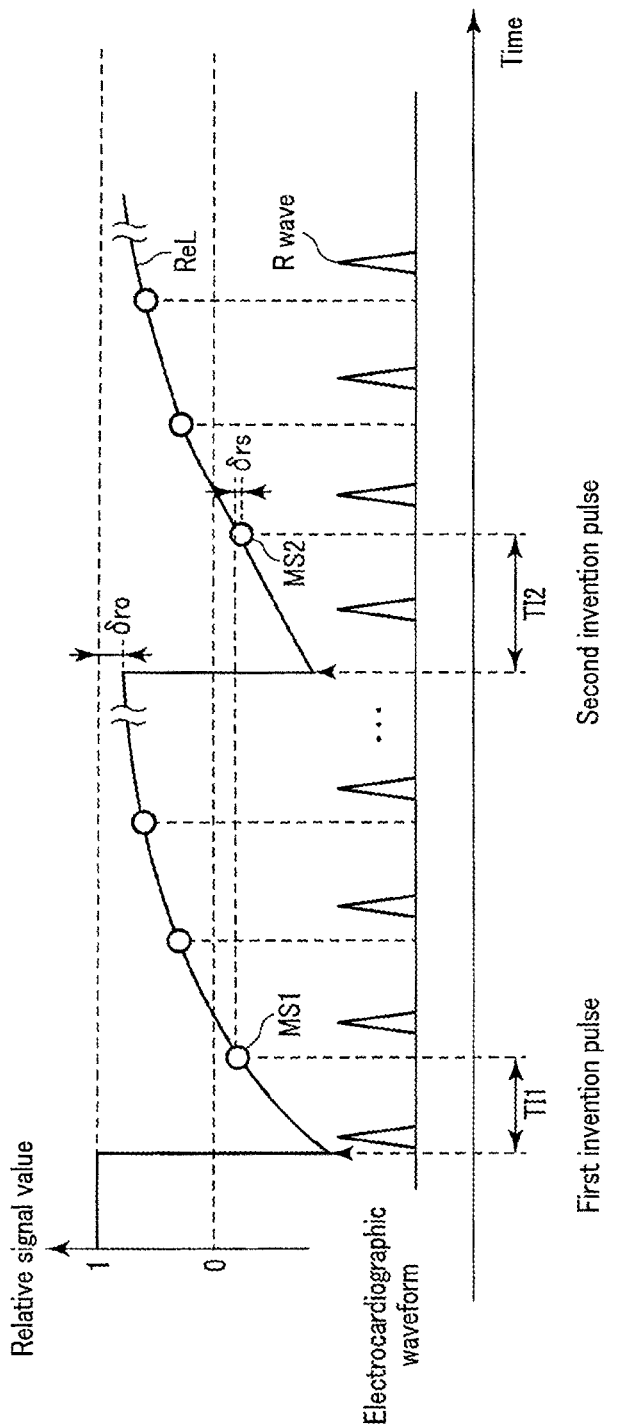
FIG. 10 is a view illustrating a relaxation curve of longitudinal magnetization in a conventional MOLLI method, along with an electrocardiographic waveform.

FIG. 9 is a view illustrating an example of a calculation result of a relative signal value in a certain pixel relating to a T1 sequence in the case of a collection pattern of "*-/*-*-*-/-*/*". As illustrated in FIG. 9, an inversion time of first imaging I1, i.e., pre-inversion imaging, executed two heartbeats prior to a first inversion pulse IR1 virtually corresponds to infinity. A pixel value of a first MR image generated by the first imaging I1 corresponds to a component $F_1$ of a vector F in the right-hand side of the objective function s' in the equation (9). Additionally, an inversion time of second imaging I2 after the first inversion pulse IR1 shown in FIG. 9 is 482 ms. A pixel value of a second MR image generated by the second imaging I2 corresponds to a component $F_2$ of the vector F in the equation (9). An inversion time of third imaging I3 after the second imaging I2 is (482+2×RR interval) ms. A pixel value of a third MR image generated by the third imaging I3 corresponds to a component $F_3$ of the vector F in the equation (9). An inversion time of fourth imaging I4 after the third imaging I3 is (482+4×RR interval) ms. A pixel value of a fourth. MR image generated by the fourth imaging I4 corresponds to a component $F_4$ of the vector F in the equation (9). An inversion time of fifth imaging I5 after a second inversion pulse IR2 is (170+RR interval) ms. A pixel value of a fifth MR image generated by fifth imaging I5 corresponds to a component. $F_5$ of the vector F in the equation (9). An inversion time of sixth imaging I6 after a third inversion pulse IR3 is 60 ms. A pixel value of a sixth MR image generated by the sixth imaging I6 corresponds to a component $F_6$ of the vector F in the equation (9).

An MR signal in a central raw of a k-space, i.e., when ky=0, most contributes to the center of contrast in an MR image. For this reason, as $g_i$ used for the calculation of the objective function, for example, in each of a plurality of collections, a relative signal value is used which is obtained at the time of collecting an MR signal (hereinafter, referred to as "center collection time point") in the center row of a k-space, i.e., ky=0. For example, when a centric order method is used for a scan sequence used in the first to the sixth imaging illustrated in FIG. 9, as $g_1$ to $g_6$ used for the calculation of an objective function, for example, a relative signal value is used at the point of starting imaging as illustrated in FIG. 9. It should be noted that a plurality of glare not limited to relative signal values at the center collection time point, and a relative signal value at discretional time points during the imaging time in each of the plurality of collections may be used as $g_1$. $F_1$ to $F_6$ and the $g_1$ to $g_6$ shown in FIG. 9 are used for calculating a function value which is a value of the objective function. The processing circuitry 131 determines a T1 value such that the function value becomes a minimum, in other words, the value of the objective function becomes a minimum. The determination of a T1 value is executed on a pixel to pixel basis.

(Step Sa7)

The processing circuitry 131 generates a T1 map by the T1 map generation function 1317, using a T1 value determined on a pixel to pixel basis. The processing circuitry 131 displays the generated T1 map on the display 127. Summarizing the processing of Step Say and Step Sa6, the processing circuitry 131 generates a T1 map representing a distribution of T1 values using MR signals collected in a plurality of collection timings and displays the generated T1 map on the display 127.

According to the configuration described above, the following effects can be obtained.

According to the MRI apparatus 1 of the embodiment, it is possible to execute a pulse sequence for collecting MR signals in a plurality of collection timings along a relaxation curve of longitudinal magnetization in synchronization with heartbeats or blood beats, to generate a T1 map representing a distribution of T1 values using the MR signals collected in the plurality of collection timings, and to execute, in the pulse sequence, collecting none of magnetic resonance signals in at least one heartbeat or at least one blood beat among a plurality of heartbeats or a plurality of blood beats following the application of an inversion pulse which inverts the polarity of longitudinal magnetization. That is, according to the MRI apparatus 1, it enables not collecting any magnetic resonance signal in at least one heartbeat or at least one blood beat among a plurality of heartbeats or a plurality of blood beats included between a first inversion pulse which inverts a polarity of the longitudinal magnetization and a second inversion pulse which is applied after application of the first inversion pulse, and collecting a magnetic resonance signal in a heartbeat subsequent to or a blood beat subsequent to the at least one heartbeat or the at least one blood beat in which no magnetic resonance signal is collected.

In addition, according to the MRI apparatus 1, with respect to a pulse sequence, it is possible to accept a setting concerning a relation among heartbeats or blood beats, collecting timings, a first inversion pulse, and a second inversion pulse from an operator. According to the MRI apparatus 1, it is possible to calculate a T1 value in each pixel in a T1 map according to the relation among the heartbeats or blood beats, collecting timings, the first inversion pulse, and the second inversion pulse in the pulse sequence executed by the sequence control unit (sequence control circuitry). According to the MRI apparatus 1, the second inversion pulse can be applied before the longitudinal magnetization completely recovers after the application of the first inversion pulsed. According to the MRI apparatus 1, it is possible to collect an MR signal before application of the first inversion pulse, as an initial collecting timing of a plurality of collection timings in a pulse sequence.

Additionally, according to the MRI apparatus 1, it is possible to set a plurality of collection timings in a pulse sequence such that a signal value of an MR signal provided with a sign is monotonously increased along the ascending order of the inversion time from the time point of application of the first inversion pulse to each of the collection timings. According to the MRI apparatus 1, when imaging is executed over three or more heartbeats or three or more blood beats following the application of a first inversion pulse in the execution of a pulse sequence, it is possible to collect none of magnetic resonance signals in at least one heartbeat or at least one blood beat of a plurality of heartbeats or a plurality of blood beats included between the point of application of the first inversion pulse and the point of application of the second inversion pulse. According to the MRI apparatus 1, when imaging is executed over three or more heartbeats or three or more blood beats following the application of a first inversion pulse in the execution of a pulse sequence, it is possible to collect none of magnetic resonance signals in a heartbeat or a blood beat immediately before a first inversion pulse, or in a heartbeat or a blood beat immediately after the first inversion pulse in the execution of a pulse sequence. According to the MRI apparatus 1, a first inversion pulse can be applied at intervals of five or less heartbeats or five or less blood beats in the execution of a pulse sequence.

Furthermore, according to the MRI apparatus 1, it is possible to calculate signal values of MR signals in a plurality of collection timings, based on a model for calculating a change in longitudinal magnetization in a relaxation process of the longitudinal magnetization, a change in the longitudinal magnetization due to a first inversion pulse and a second inversion pulse, a change in the longitudinal magnetization due to an RF pulse used for collection of MR signals, and a change in the longitudinal magnetization due to a stabilization pulse applied to a subject for stabilization of MR signals immediately before application of the RF pulse and to calculate T1 values so as to match the calculated signal values for pixel values in a plurality of MR images generated based on the collected MR signals.

Based on the foregoing, according to the MRI apparatus 1 of the embodiment, the calculation is executed in a state where a temporal change of signal values by read-out of an image (collection of MR signals) and an effect brought about by performing application of an inversion pulse before the longitudinal magnetization completely recovers are incorporated into a simulation, and thus a T1 value can be calculated using a plurality of MR images based on an MR signal collected by the execution of a T1 sequence as illustrated in FIG. 4. With this configuration, the MRI apparatus 1 can determine a T1 value with high accuracy in a short period of breath-hold without extending the period of breath-hold, i.e., in a short time. In addition, the MRI apparatus 1 can determine a T1 value relative to a wide range of heart rates as shown in FIG. 4. Furthermore, according to the MRI apparatus 1, it is possible to increase the number of signal values used in the calculation of a T1 value by pre-inversion imaging and to determine a T1 value with high accuracy.

When the technical idea of the MRI apparatus 1 is realized by cloud computing or the like as an application example of the embodiment, a server on the internet includes, for example, the storage apparatus 129 and the processing circuitry 131 in the configuration view of FIG. 1. In this case, the T1 map generation function 1317, etc. can be realized by installing a program for executing the function (medical processing program) in the processing circuitry 131 of the server and developing the program on the memory. Furthermore, the T1 map generation processing described in the embodiment may also be realized as a magnetic resonance imaging method.

(Variation)

Figure 12:
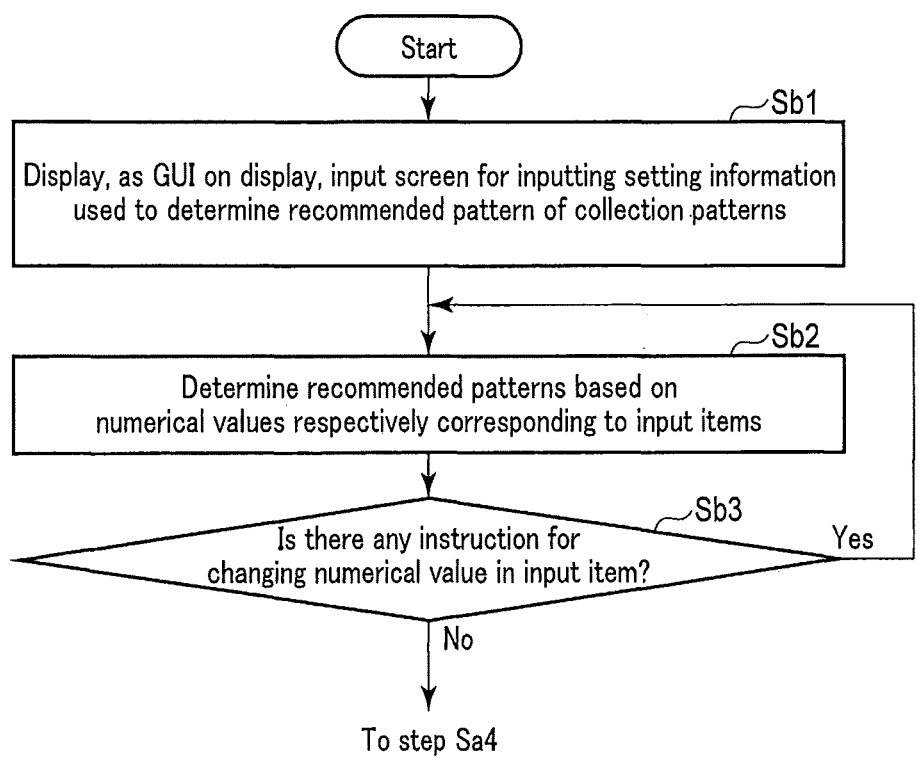
FIG. 12 is a view illustrating an example of T1 map generation processing in a variation of the embodiment.

A main difference between a variation and the embodiment is in the processing executed in Step Sa1 to Step Sa3 in the procedure of the T1 map generation processing. Hereinafter, processing contents (Step Sb1 to Step Sb3) respectively different from the processing contents of Step Sa1 to Step Sa3 will be described. FIG. 12 is a view illustrating an example of the T1 map generation processing in the application of the embodiment.

(Step Sb1)

The processing circuitry 131 displays, for example, as a GUI (graphical user interface) on the display 127 by the T1 sequence determining function 1315, an input screen for inputting information (hereinafter, referred to as "setting information") used for specifying collection patterns recommended by the operator (hereinafter, referred to as "recommended patterns") among a plurality of collection patterns stored in the storage apparatus 129. The setting information includes at least one setting parameter relating to the setting of a pulse sequence (T1 sequence). The setting parameters are, for example, a flip angle of an RF pulse in a pulse sequence, a T1 value relating to an imaging target (hereinafter, referred to as "target T1 value), and the like. The GUI is provided with input items for the setting parameters. It should be noted that the input screen may include a GUI capable of discretionally adjusting an inversion pulse, collection timings, non-read-out periods, and the like. In this case, the collection patterns can be discretionally adjusted as desired by the operator.

It should be noted that the setting information may further include, as an input item, a heart rate or a pulse rate. The heart rate or pulse rate as an input item is not limited to a single value, and the input item may be a heart rate range or a pulse rate range defined by an upper limit value and a lower limit value. Hereinafter, to specifically describe the variation, it is assumed that the setting information includes, as a plurality of input items, a heart rate (bpm), a target T1 value (ms), and a flip angle (degree).

The interface 125 acquires a heart rate of a subject P from an electrocardiogram. It should be noted that the interface 125 may acquire a pulse rate of a subject P from a pulse counter.

The display 127 displays the input screen. Specifically, the display 127 displays an input screen in a state where various numerical values can be entered in each of the plurality of input items on the input screen by the operator. It should be noted that the display 127 may display a plurality of input candidates relating to the input items in accordance with an input item at which a cursor is positioned, for example, in a pull-down menu form.

In addition, the display 127 may display, in the input item of the heart rate on the input screen, an average value of heart rates acquired. It should be noted that the display 127 may display, in the input item of the heart rate on the input screen, a heart rate range based on the acquired heart rates. At this time, the heart rate range corresponds to, for example, a 95% confidence interval based on the plurality of heart rates acquired over a predetermined period. Also, the display 127 may display, in the input item of a pulse rate on the input screen, an average value of pulse rates acquired. It should be noted that the display 127 may display, in the input item of the pulse rate on the input screen, a pulse rate range based on the acquired pulse rates. At this time, the pulse rate range corresponds to, for example, a 95% confidence interval based on the plurality of pulse rates acquired over a predetermined period. It should be noted that the heart rate range and the pulse rate range are not limited to 95% confidence intervals, and these ranges may be set discretionally. If a flip angle is entered as an imaging condition, the display 127 may display, in the input item of a flip angle on the input screen, a flip angle in the imaging condition.

If an imaging target (e.g., an organ, etc.) is entered as an imaging condition, the processing circuitry 131 may determine a T1 value by the T1 sequence determining function 1315, based on a correspondence list for an imaging target (hereinafter, referred to as "target T1 value correspondence list") and an imaging target entered. At that time, the processing circuitry 131 may display the determined T1 value in the input item of a target T1 value on the input screen of the display 127. The target T1 value correspondence list is preliminarily stored in the storage apparatus 129.

The interface 125 inputs a numerical value for each of a plurality of input items on the input screen by an instruction of the operator. The interface 125 outputs a plurality of numerical values in the plurality of input items to the processing circuitry 131.

(Step Sb2)

The processing circuitry 131 determines, by the T1 sequence determining function 1315, at least one recommended sequence which is recommended as a pulse sequence (T1 sequence) based on setting information including at least one setting parameter relating to the setting of the pulse sequence. Specifically, the processing circuitry 131 determines a plurality of recommended patterns respectively corresponding to a plurality of recommended sequences, based on a plurality of numerical values respectively corresponding to the plurality of input items. For example, if 60 is entered in the input item of heart rate, the processing circuitry 131 identifies 10 collection patterns included in "Wide range (50 to 100 bpm)" and "Low heart rate (50 to 75 bpm)" among the plurality of collection patterns illustrated in FIG. 4. Next, the processing circuitry 131 executes a simulation using the flip angle in the input item for each of the identified 10 collection patterns. The processing circuitry 131 calculates a T1 value by execution of the simulation. The processing circuitry 131 determines, as recommended patterns, a plurality of collection patterns, which are close to the target T1 value, from among the T1 values (hereinafter, referred to as "estimated T1 value") calculated for each of the identified 10 collection patterns. It should be noted that the processing circuitry 131 may calculate T1 recovery curves respectively corresponding to the plurality of recommended patterns by using each of a plurality of estimated T1 values. At this time, the processing circuitry 131 may generate a graph (hereinafter, referred to as "T1 recovery graph") representing T1 recovery curves respectively corresponding to the plurality of recommended patterns.

The processing circuitry 131 calculates the accuracy of T1 values by the T1 sequence determining function 1315 by changing the setting parameters, based on a recommended sequence and the setting parameters. Specifically, the processing circuitry 131 executes a simulation using a flip angle in the input item for each of the plurality of recommended patterns by changing the heart rate. The processing circuitry 131 calculates relative errors of T1 values relative to the plurality of heart rates as the accuracy of T1 values, by executing the simulation. In each of the recommended patterns, the relative error of T1 value relative to the plurality of heart rates represents a degree of robustness (hereinafter, referred to as "heartbeat robustness") of the T1 value relative to the heartrate. At this time, the processing circuitry 131 may generate a graph (hereinafter, referred to as "accuracy heartbeat graph") representing the heartbeat robustness relative to each of the plurality of recommended patterns. In addition, the processing circuitry 131 may generate a list (hereinafter, referred to as "heartbeat robustness list") representing the heartbeat robustness relative to each of the plurality of recommended patterns, instead of the accuracy heartbeat graph.

Furthermore, the processing circuitry 131 may execute a simulation using a flip angle in the input item by the T1 sequence determining function 315 by changing the T1 value relative to each of the recommended patterns. The processing circuitry 131 calculates a relative error of a T1 value relative to a plurality of T1 values as the accuracy of the plurality of T1 values by executing the simulation. In each of the recommended patterns, the relative error of a T1 value relative to the plurality of T1 values indicates a degree of T1 value robustness (hereinafter, referred to as "T1 robustness") relative to the T1 value. At this time, the processing circuitry 131 may generate a graph (hereinafter, referred to as "accuracy T1 graph") indicating the T1 robustness relative to each of the plurality of recommended patterns. In addition, the processing circuitry 131 may generate a list (hereinafter, referred to as "T1 robustness list") indicating the T1 robustness relative to each of the plurality of recommended patterns.

Furthermore, the processing circuitry 131 may execute a simulation by the T1 sequence determining function 1315, by changing a flip angle in the input item relative to each of the plurality of recommended patterns. The processing circuitry 131 calculates a relative error of a T1 value relative to a plurality of flip angles as the accuracy of the T1 value. In each of the recommended patterns, the relative error of a T1 value relative to a plurality of flip angles indicates a degree of the robustness (hereinafter, referred to as "flip robustness") of T1 value relative to flip angles. At that time, the processing circuitry 131 may generate a graph (hereinafter, referred to as "accuracy flip graph") indicating the flip robustness relative to each of the plurality of recommended patterns. Also, the processing circuitry 131 may generate a list (hereinafter, referred to as "flip robustness list") indicating the flip robustness relative to each of the plurality of recommended patterns, instead of the accuracy flip graph.

The processing circuitry 131 determines, by the T1 sequence determining function 1315, a period of breath-hold, an imaging time, and the like in each of the recommended patterns, based on the number of inversion times, a collection heart rate, a plurality of TIs in each of the recommended patterns. The processing circuitry 131 generates a list (hereinafter, referred to as "selection guideline list") representing a period of breath-hold, an imaging time, heartbeat robustness, an estimated T1 value, and the like.

Figure 13:
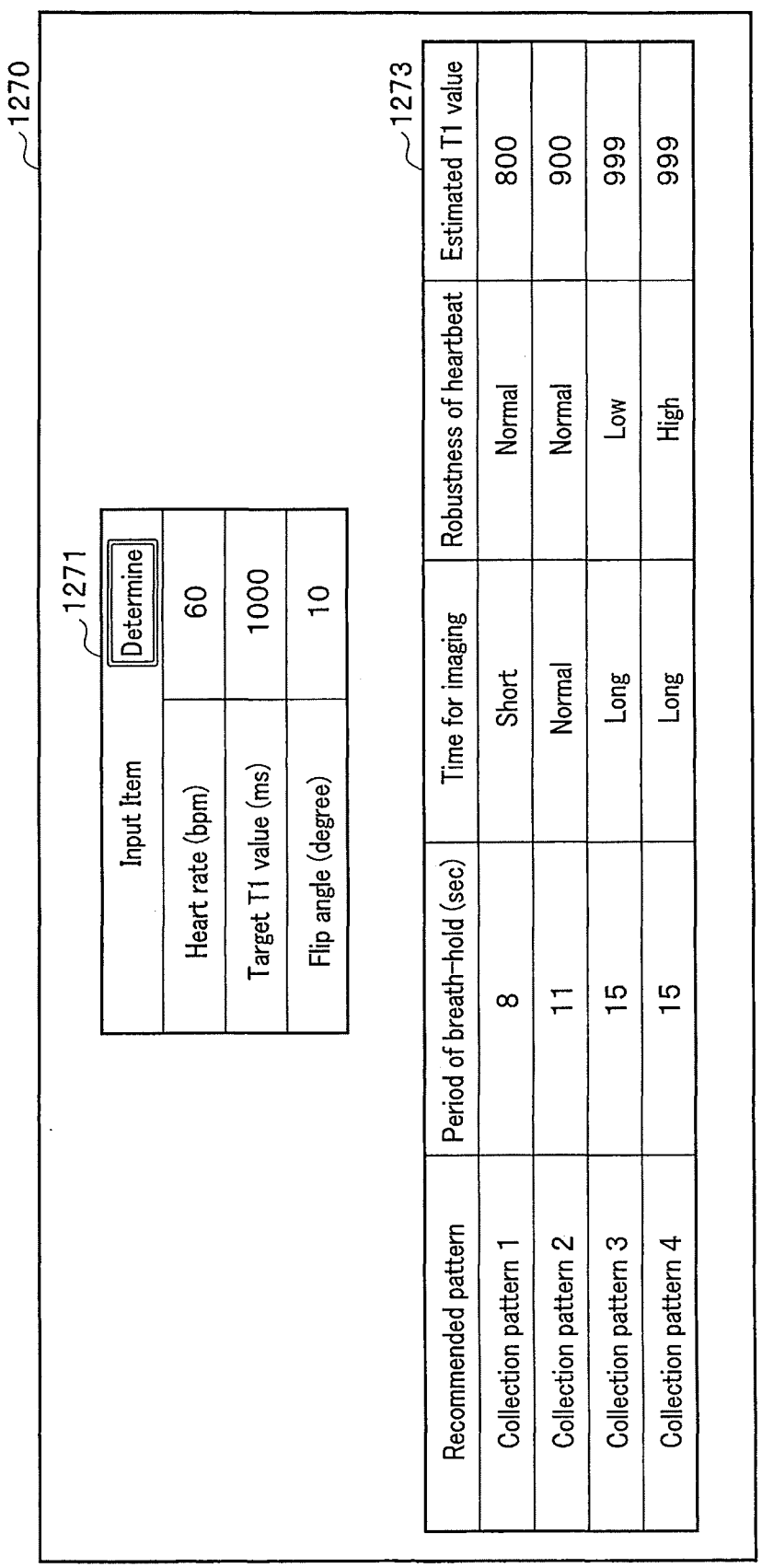
FIG. 13 is a view illustrating an example of an entered GUI and a selection guideline list displayed on a display screen of a display, in the variation of the embodiment.

The processing circuitry 131 displays, on the display 127, a selection guideline list along with a GUI indicating a numerical value entered for each of the plurality of input items (hereinafter, referred to as "entered GUI"). FIG. 13 is a view illustrating an example of an entered GUI 1271 and a selection guideline list 1273 displayed on a display screen 1270 of the display 127. When numerical values are entered in the plurality of input items and a "Determine" button is pressed down, the selection guideline list 1273 is displayed along with the entered GUI 1271 on the display 127 as illustrated on the display screen 1270 in FIG. 13. Collection patters 1 to 4 in the selection guideline list in FIG. 13 may be displayed, for example, in the form of using symbols as shown in FIG. 4.

The display 127 displays a recommended sequence, setting parameters, and the accuracy of the T1 value. For example, the display 127 displays the selection guideline list 1273 and the entered GUI 1271. It should be noted that the display 127 may display at least one of a T1 recovery graph, an accuracy heartbeat graph, an accuracy T1 graph, and an accuracy flip graph in addition to the selection guideline list 1273 and the entered GUI 1271. It should be noted that the display 127 may display, in addition to the selection guideline list 1273 and the entered GUI 1271, a heartbeat robust list instead of the accuracy heartbeat graph, may display a T1 robust list instead of the accuracy T1 graph, and may display a flip robustness list instead of the accuracy flip graph.

Figure 14:
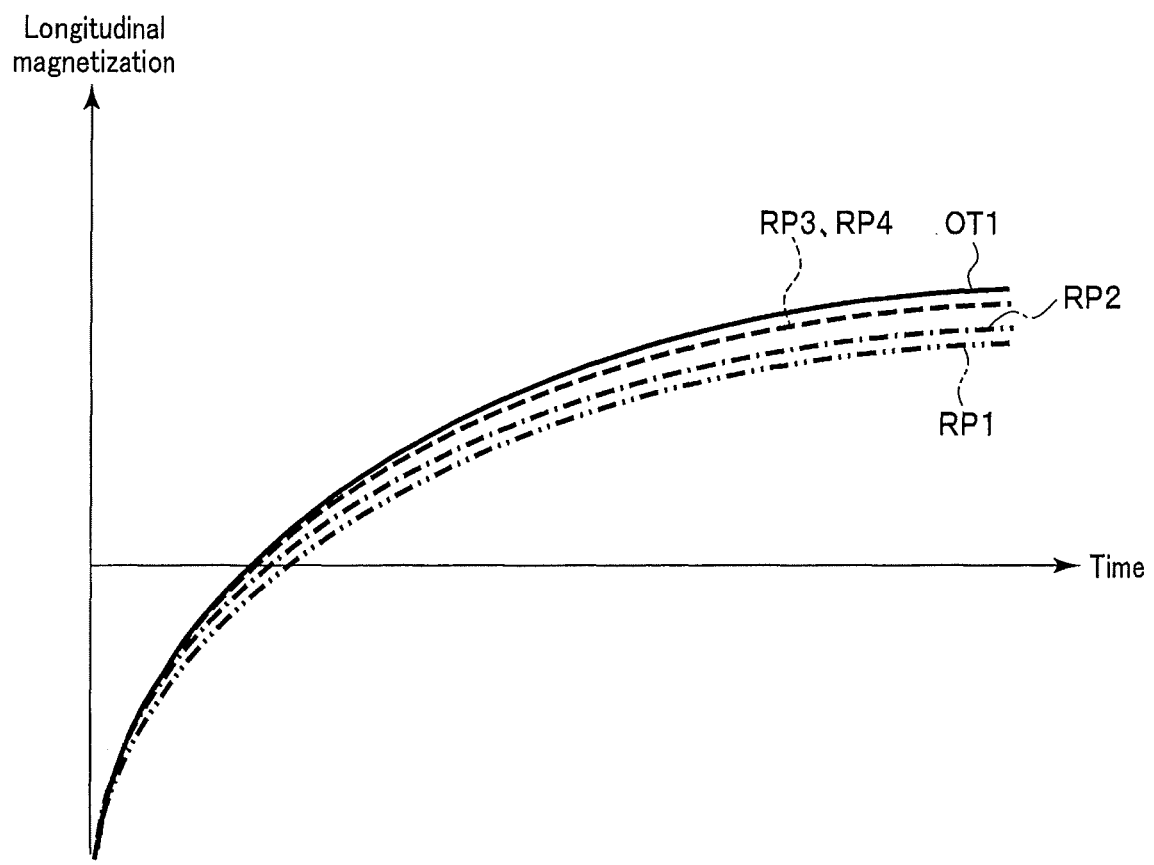
FIG. 14 is a view illustrating an example of a T1 recovery graph in the variation of the embodiment.

FIG. 14 is a view illustrating an example of a T1 recovery graph. As illustrated in FIG. 14, a plurality of T1 recovery curves respectively corresponding to the plurality of recommended patterns are shown in the T1 recovery graph. OT1 shown in FIG. 14 indicates a T1 recovery curve generated based on a target T1 value. RP1 shown in FIG. 14 indicates a T1 recovery curve generated based on the estimated T1 value concerning the collection pattern 1 among the plurality of collection patterns in the selection guideline list 1273. RP2 shown in FIG. 14 indicates a T1 recovery curve generated based on an estimated T1 value concerning the collection pattern 2 among the plurality of collection patterns in the selection guideline list 1273. RP3 and RP4 shown in FIG. 14 respectively indicate a T1 recovery curve generated based on the estimated T1 value concerning the collection pattern 3 among the plurality of collection patterns in the section guideline list 1273 and a T1 recovery curve generated based on the estimated T1 value concerning the collection pattern 4 among the plurality of collection patterns in the section guideline list 1273.

Figure 15:
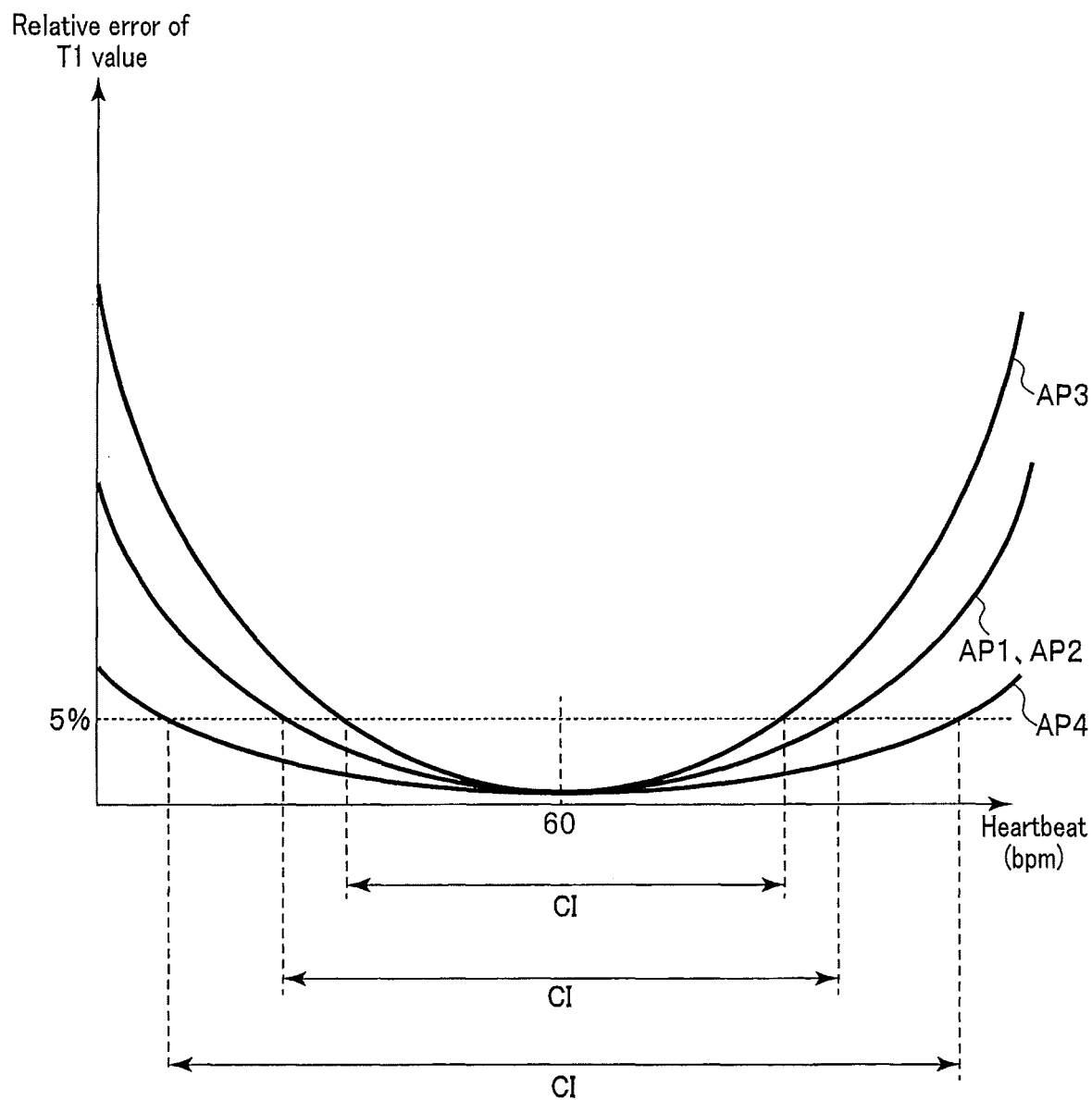
FIG. 15 is a view illustrating an example of an accuracy heartbeat graph in the variation of the embodiment.

FIG. 15 is a view illustrating an example of an accuracy heartbeat graph. AP1 and AP2 shown in FIG. 15 respectively indicate the heartbeat robustness concerning the collection pattern 1 among the plurality of recommended patterns in the selection guideline list 1273 and the heartbeat robustness concerning the collection pattern 2 among the plurality of recommended patterns in the selection guideline list 1273. AP3 shown in FIG. 15 indicates the heartbeat robustness concerning the collection pattern 3 among the plurality of recommended patterns in the selection guideline list 1273. AP4 shown in FIG. 15 indicates the heartbeat robustness concerning the collection pattern 4 among the plurality of recommended patterns in the selection guideline list 1273. An interval CI shown in FIG. 15 indicates a 95% confidence interval. In the 95% confidence interval, an upper limit heart rate (not shown) and a lower limit heart rate (not shown) may be displayed which are not shown in FIG. 15. It should be noted that the display of the confidence interval in the accuracy heartbeat graph is not limited to 95% and may be set discretionally. As illustrated in FIG. 13 and FIG. 15, the heartbeat robustness AP4 concerning the collection pattern 4 has high robustness relative to the heart rate as compared with those of the other recommended patterns.

Figure 16:
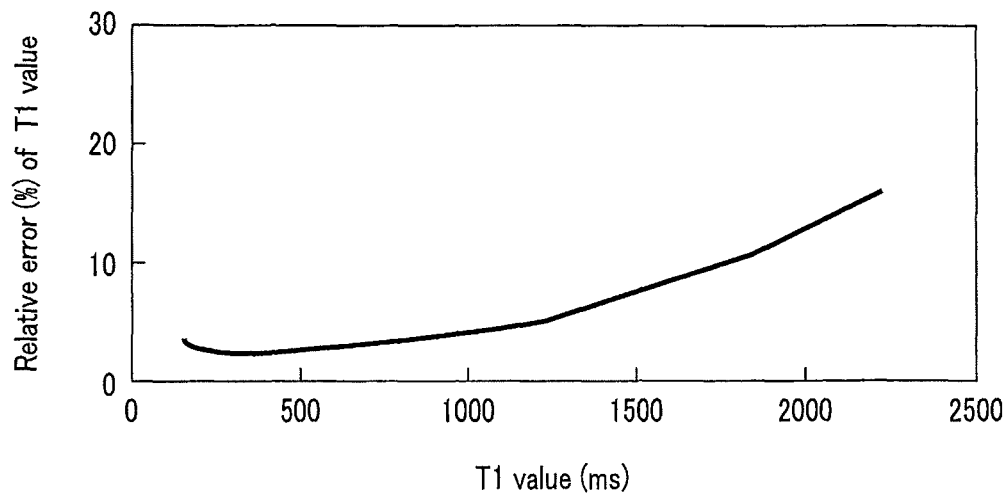
FIG. 16 is a view illustrating an example of an accuracy T1 graph in the variation of the embodiment.

FIG. 16 is a view illustrating an example of an accuracy T1 graph. The accuracy T1 graph indicates the T1 robustness concerning a particular collection pattern among the plurality of recommended patterns in the selection guideline list 1273. In addition, the accuracy T1 graph indicates that T1 values can be measured using a particular collection pattern to a T1 value of 1700 ms within a 10% error. Also, the accuracy T1 graph indicates that if the T1 value exceeds 1700 ms, the accuracy of T1 values measured using the particular collection pattern degrades.

Figure 17:
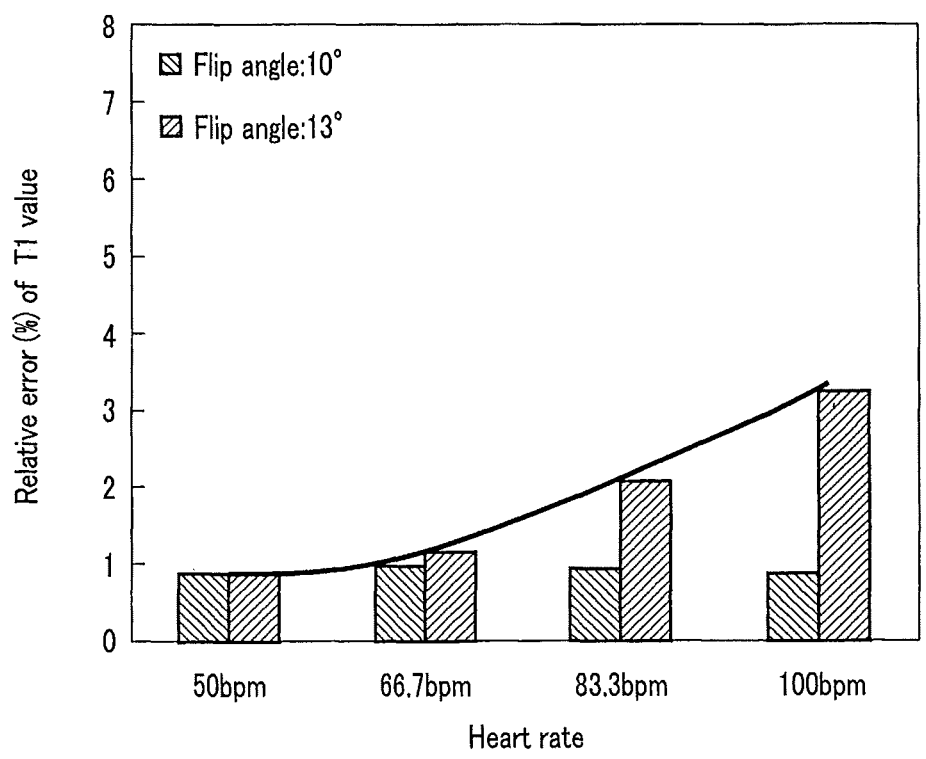
FIG. 17 is a view illustrating an example of an accuracy flip graph according to a heart rate in the variation of the embodiment.

FIG. 17 is a view illustrating an example of an accuracy flip graph according to a heart rate. The accuracy flip graph illustrated in FIG. 17 indicates the flip robustness concerning a particular collection pattern of the plurality of recommended patterns in the selection guideline list 1273, for example, the third collection pattern from the top (Range of heart rate: 50 to 100 bpm) of the collection patterns described in FIG. 4 for each of the heart rates. The accuracy flip graph indicates that even if the collection pattern is included in the wide range of heart rates of 50 to 100 bpm, the accuracy of a T1 value to be measured may degrade depending on a flip angle adopted.

(Step Sb3)

If there is an instruction for changing an input item via the interface 125, the processing circuitry 131 repeats, by the T1 sequence determining function 1315, the processing of Step Sa1 and the processing Sb2 in this variation (Step Sb3: Yes). When a collection pattern among the plurality of recommended patterns in the selection guideline list 1273 is selected via the interface 125, the processing circuitry 131 determines a T1 sequence corresponding to the selected collection pattern (Step Sb3: No). Next, the processing circuitry 131 outputs the determined T1 sequence to the sequence control circuitry 121. In Step Sa4 following this step, the sequence control circuitry 121 collects MR signals in accordance with the determined T1 sequence. The processing subsequent to this processing is identical to that of the embodiment, and thus explanations thereof are omitted.

According to this variation, the following effects can be obtained in addition to the effects described in the embodiment.

According to the MRI apparatus 1, it is possible to determine at least one recommended sequence which is recommended as a pulse sequence, based on setting information including at least one setting parameter relating to setting of a pulse sequence, to calculate the accuracy of the T1 value by changing the setting parameter, based on the recommended sequence and the setting parameter, and to display the recommended sequence, the setting parameter, and the accuracy. Furthermore, according to the MRI apparatus 1, it is possible to use, as the accuracy of T1 value, a graph or a list showing a relative error of the T1 value relative to the setting parameter, using, as a setting parameter, at least one of heartbeats or blood beats, a T1 value, and a flip angle of an RF pulse in the pulse sequence.

Based on the above, according to the MRI apparatus 1, the operator can select a collection pattern and generate a T1 map with high accuracy T1 values by using a selected collection pattern in consideration of setting parameters, heartbeat robustness, T1 robustness, flip robustness, etc. which serve as guidelines for selecting a collection pattern.

According to a magnetic resonance imaging apparatus 1 such as the embodiment described above, it is possible to generate a T1 map having highly accurate T1 values.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A magnetic resonance imaging apparatus comprising:
sequence control circuitry configured to execute a pulse sequence for collecting magnetic resonance signals in a plurality of collection timings along a relaxation curve of longitudinal magnetization in synchronization with heartbeats or blood beats; and
processing circuitry configured to generate a T1 map representing a distribution of T1 values by using the magnetic resonance signals collected in the plurality of collection timings,
wherein the pulse sequence is set so as not to collect any magnetic resonance signal in at least one heartbeat or at least one blood beat among a plurality of heartbeats or a plurality of blood beats included between a first inversion pulse which inverts a polarity of the longitudinal magnetization and a second inversion pulse which is applied after application of the first inversion pulse, and so as to collect a magnetic resonance signal in a heartbeat subsequent to or a blood beat subsequent to the at least one heartbeat or the at least one blood beat in which no magnetic resonance signal is collected.

2. The magnetic resonance imaging apparatus according to claim 1, further comprising:
an interface which accepts, from an operator, a setting concerning a relation among the plurality of heartbeats or the plurality of blood beats, the plurality of collection timings, the first inversion pulse, and the second inversion pulse.

3. The magnetic resonance imaging apparatus according to claim 1, wherein the processing circuitry is configured to calculate a T1 value of each pixel in the T1 map in accordance with the relation among the plurality of heartbeats or the plurality of blood beats, the plurality of collection timings, the first inversion pulse, and the second inversion pulse in the pulse sequence executed by the sequence control circuitry.

4. The magnetic resonance imaging apparatus according to claim 1, wherein the second inversion pulse is applied before the longitudinal magnetization completely recovers after the application of the first inversion pulse.

5. The magnetic resonance imaging apparatus according to claim 1, wherein the pulse sequence is set, as an initial collection timing of the plurality of collection timings, so as to collect a magnetic resonance signal before the application of the first inversion pulse.

6. The magnetic resonance imaging apparatus according to claim 1, wherein the plurality of collection timings in the pulse sequence are set in an ascending order of an inversion time from a time point of the application of the first inversion pulse to each of the plurality of collection timings such that a signal value of a magnetic resonance signal provided with a sign is monotonously increased.

7. The magnetic resonance imaging apparatus according to claim 1, wherein the pulse sequence is set, when imaging is executed over three or more heartbeats or three or more blood beats following the application of the first inversion pulse, so as not to collect any magnetic resonance signal in at least one heartbeat or at least one blood beat among the plurality of heartbeats or the plurality of blood beats included between a time point of the application of the first inversion pulse and a time point of application of the second inversion pulse.

8. The magnetic resonance imaging apparatus according to claim 1, wherein the pulse sequence is set so as not to collect any magnetic resonance signal in a heartbeat or a blood beat immediately before the first inversion pulse, or a heartbeat or a blood beat immediately after the first inversion pulse.

9. The magnetic resonance imaging apparatus according to claim 8, wherein the pulse sequence is set so as to apply the first inversion pulse at intervals of five heartbeats or less, or five blood beats or less.

10. The magnetic resonance imaging apparatus according to claim 1, wherein the processing circuitry is configured to:
calculate signal values of magnetic resonance signals in the plurality of collection timings, based on a model for calculating a change in the longitudinal magnetization in a relaxation process of the longitudinal magnetization, a change in the longitudinal magnetization due to the first inversion pulse and the second inversion pulse, a change in the longitudinal magnetization by an RF pulse used for collection of the magnetic resonance signals, and a change in the longitudinal magnetization due to a pulse applied to a subject for stabilization of the magnetic resonance signals immediately before application of the RF pulse, and
calculate T1 values such that the calculated signal value is matched with a pixel value in a plurality of magnetic resonance images generated based on the collected magnetic resonance signals.

11. The magnetic resonance imaging apparatus according to claim 1, wherein the processing circuitry is configured to:
determine at least one recommended sequence, which is recommended as the pulse sequence, based on setting information including at least one setting parameter relating to the setting of the pulse sequence;
calculate the accuracy of the T1 value by changing the setting parameter, based on the recommended sequence and the setting parameter; and
wherein the magnetic resonance imaging apparatus further comprises a display that displays the recommended sequence, the setting parameter, and the accuracy.

12. The magnetic resonance imaging apparatus according to claim 11, wherein the setting parameter is at least one of the heartbeats or the blood beats, the T1 value, and a flip angle of an RF pulse in the pulse sequence, and
the accuracy is represented by a graph or a list representing a relative error of the T1 value relative to the setting parameter.

13. A magnetic resonance imaging method comprising:
executing a pulse sequence for collecting a magnetic resonance signal in a plurality of collection timings along a relaxation curve of longitudinal magnetization in synchronization with heartbeats or blood beats, and generating a T1 map representing a distribution of T1 values by using magnetic resonance signals collected in the plurality of collection timings, wherein the pulse sequence is set so as not to collect any magnetic resonance signal in at least one heartbeat or at least one blood beat among a plurality of heartbeats or a plurality of blood beats included between a first inversion pulse which inverts a polarity of the longitudinal magnetization and a second inversion pulse which is applied after application of the first inversion pulse, and so as to collect a magnetic resonance signal in a heartbeat subsequent to or a blood beat subsequent to the at least one heartbeat or the at least one blood beat in which no magnetic resonance signal is collected.

14. The method according to claim 13, further comprising:

accepting, from an operator, a setting concerning a relation among the plurality of heartbeats or the plurality of blood beats, the plurality of collection timings, the first inversion pulse, and the second inversion pulse.

15. The method according to claim 13, calculating the T1 value of each pixel in the T1 map in accordance with the relation among the plurality of heartbeats or the plurality of blood beats, the plurality of collection timings, the first inversion pulse, and the second inversion pulse in the pulse sequence executed by the sequence control circuitry.

16. The method according to claim 13, wherein executing the pulse sequence comprises applying the second inversion pulse before the longitudinal magnetization completely recovers after the application of the first inversion pulse.

17. The method according to claim 13, wherein the pulse sequence is set, as an initial collection timing of the plurality of collection timings, so as to collect a magnetic resonance signal before the application of the first inversion pulse.

18. The method according to claim 13, wherein the plurality of collection timings in the pulse sequence are set in an ascending order of an inversion time from a time point of the application of the first inversion pulse to each of the plurality of collection timings such that a signal value of a magnetic resonance signal provided with a sign is monotonously increased.

19. The method according to claim 18, wherein the pulse sequence is set so as to apply the first inversion pulse at intervals of five heartbeats or less or five blood beats or less.

20. The method according to claim 13, further comprising:

calculating signal values of magnetic resonance signals in the plurality of collection timings, based on a model for calculating a change in the longitudinal magnetization in a relaxation process of the longitudinal magnetization, a change in the longitudinal magnetization due to the first inversion pulse and the second inversion pulse, a change in the longitudinal magnetization by an RF pulse used for collection of the magnetic resonance signals, and a change in the longitudinal magnetization due to a pulse applied to a subject for stabilization of the magnetic resonance signals immediately before application of the RF pulse, and calculating T1 values such that the calculated signal value is matched with a pixel value in a plurality of magnetic resonance images generated based on the collected magnetic resonance signals.

\* \* \* \* \*